United States Patent
Stevenson et al.

(10) Patent No.: US 11,730,210 B2
(45) Date of Patent: Aug. 22, 2023

(54) WIRELESS ANTI-STATIC DEVICE FOR ESD MITIGATION

(71) Applicant: IONA Tech LLC, Telluride, CO (US)

(72) Inventors: Daan Stevenson, Telluride, CO (US); Jonathan Tapson, Telluride, CO (US)

(73) Assignee: IONA Tech LLC, Telluride, CO (US)

( * ) Notice: Subject to any disclaimer, the term of this patent is extended or adjusted under 35 U.S.C. 154(b) by 0 days.

(21) Appl. No.: 17/637,196

(22) PCT Filed: Aug. 13, 2021

(86) PCT No.: PCT/US2021/045850
§ 371 (c)(1),
(2) Date: Feb. 22, 2022

(87) PCT Pub. No.: WO2022/040024
PCT Pub. Date: Feb. 24, 2022

(65) Prior Publication Data
US 2022/0395033 A1  Dec. 15, 2022

Related U.S. Application Data

(63) Continuation of application No. 63/172,893, filed on Apr. 9, 2021, and a continuation of application No. 63/067,089, filed on Aug. 18, 2020.

(51) Int. Cl.
*A41D 13/008* (2006.01)
*A41D 1/00* (2018.01)
(Continued)

(52) U.S. Cl.
CPC .......... *A41D 13/008* (2013.01); *A41D 1/002* (2013.01); *G06F 1/1656* (2013.01); *H05F 3/00* (2013.01)

(58) Field of Classification Search
CPC .......... A41D 13/008; A41D 1/00; H05F 3/00; H05F 3/06; A61N 1/14
(Continued)

(56) References Cited

U.S. PATENT DOCUMENTS

| 3,711,743 A | 1/1973 | Bolasny |
| 4,186,421 A | 1/1980 | Twitchett |

(Continued)

FOREIGN PATENT DOCUMENTS

| CN | 1271247 A | 10/2000 |
| CN | 102591190 A | 7/2012 |

(Continued)

OTHER PUBLICATIONS

Kari Rodriquez, "International Search Report and Written Opinion Regarding International Patent Application No. PCT/US21/45850", dated Jan. 13, 2022, pp. 48, Published in: US.

(Continued)

*Primary Examiner* — Danny Nguyen
(74) *Attorney, Agent, or Firm* — Neugeboren O'Dowd PC

(57) ABSTRACT

A wireless anti-static device is disclosed, including an electronic sensing circuit that measures the polarity and electrostatic potential of the subject relative to its surroundings. Ion guns of positive and negative polarities are able to transfer an arbitrary quantity and polarity of charge from the subject by ejecting ionized air molecules into the surrounding environment. A control unit is programmed to trigger the appropriate ion gun when a corresponding charge is measured on the body, in order to continually maintain the net charge on the body below a desired threshold. The subject is thus effectively grounded relative to its environment without requiring physical tethers to ground.

27 Claims, 15 Drawing Sheets

(51) Int. Cl.
*G06F 1/16* (2006.01)
*H05F 3/00* (2006.01)

(58) Field of Classification Search
USPC .................................................. 361/231, 232
See application file for complete search history.

(56) References Cited

U.S. PATENT DOCUMENTS

| | | | |
|---|---|---|---|
| 6,137,660 A | 10/2000 | Partee et al. | |
| 6,419,171 B1 * | 7/2002 | Takayanagi | H05F 3/04 239/270 |
| 6,785,111 B1 * | 8/2004 | Osborne | G01R 29/12 361/170 |
| 7,085,120 B2 | 8/2006 | Kraz et al. | |
| 8,730,641 B2 | 5/2014 | Fukada | |
| 8,797,704 B2 | 8/2014 | Ishii et al. | |
| 10,948,976 B1 * | 3/2021 | Whitmire | G06F 3/016 |
| 2003/0071628 A1 | 4/2003 | Zank et al. | |
| 2013/0096825 A1 | 4/2013 | Mohanty | |
| 2018/0297722 A1 | 10/2018 | Agathon-Burton et al. | |
| 2021/0243874 A1 * | 8/2021 | Okazaki | H04L 67/12 |

FOREIGN PATENT DOCUMENTS

| | | |
|---|---|---|
| CN | 202486509 U | 10/2012 |
| JP | P2006114255 A | 4/2006 |
| JP | 2011151039 A | 8/2011 |
| WO | 2018052229 A1 | 3/2018 |
| WO | 2019216129 A1 | 11/2019 |

OTHER PUBLICATIONS

Mouratidis et al., "Aircraft Charging Using Ion Emission for Lightning Strike Mitigation", Feb. 1, 2019, pp. 39-78, Publisher: Massachusetts Institute of Technology.

* cited by examiner

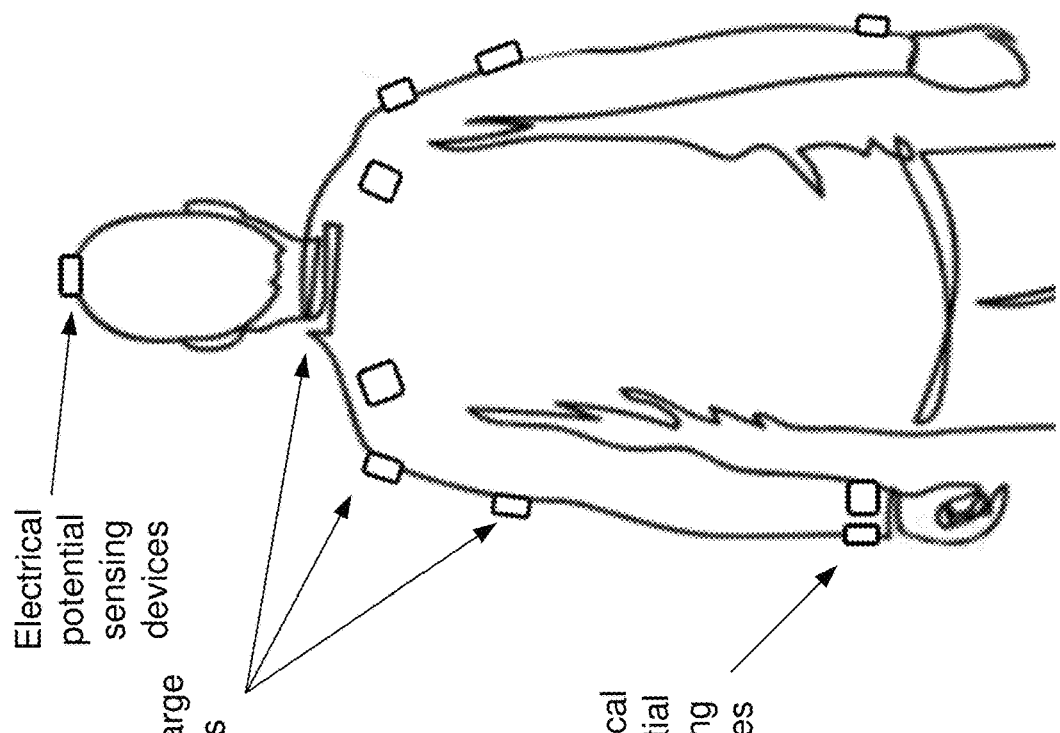
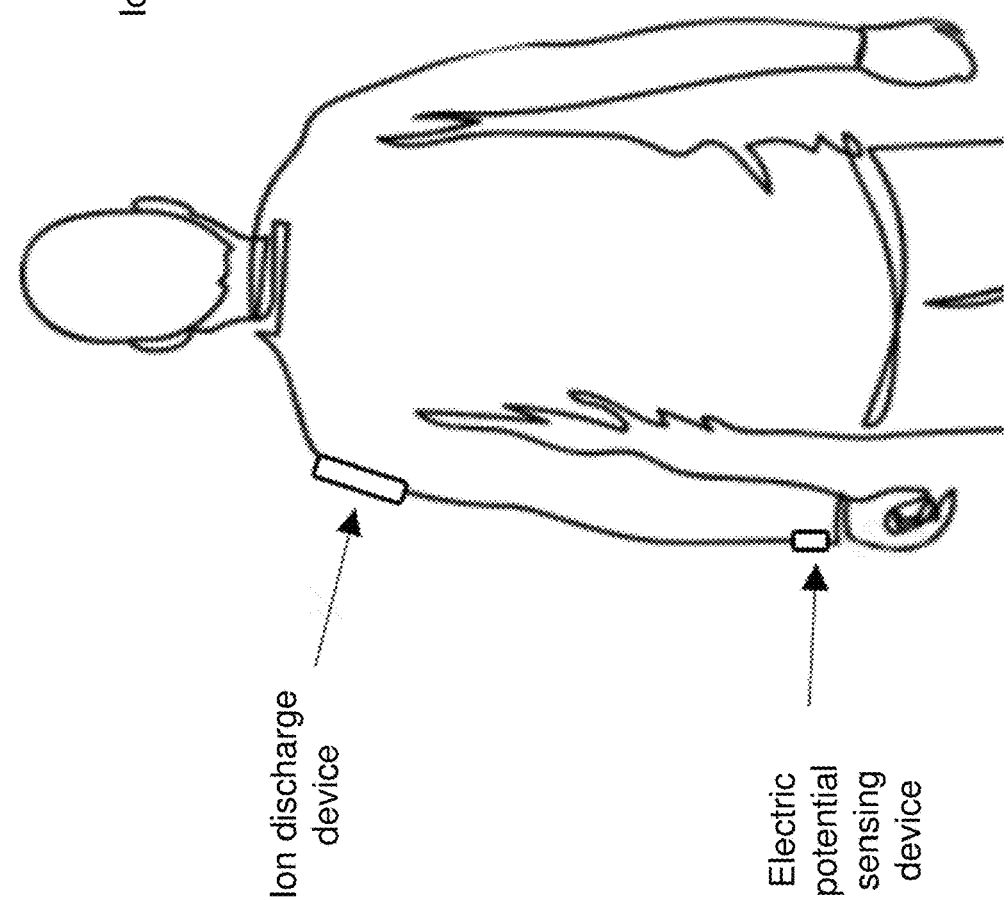
FIG. 12B
FIG. 12A

WIRELESS ANTI-STATIC DEVICE FOR ESD MITIGATION

CLAIM OF PRIORITY UNDER 35 U.S.C. § 119

The present application for patent claims priority to Provisional Application No. 63/172,893 entitled "WIRELESS ANTI-STATIC DEVICE FOR ESD MITIGATION" filed Apr. 9, 2021, and claims priority to Provisional Application No. 63/067,089 entitled "WIRELESS ANTI-STATIC DEVICE FOR ESD MITIGATION" filed Aug. 18, 2020, and assigned to the assignee hereof and hereby expressly incorporated by reference herein.

GOVERNMENT SUPPORT CLAUSE

This invention was made with government support under Award #2014652 by the National Science Foundation. The government has certain rights in the invention.

FIELD OF THE DISCLOSURE

The present disclosure relates generally to electrostatic discharge (ESD) mitigation. In particular, but not by way of limitation, the present disclosure relates to systems, methods and apparatuses for a wearable ESD mitigation device that measures the electrostatic charge on a body and actively controls its electrostatic charge by expelling excess charge from the body via charged ionic air particles.

DESCRIPTION OF RELATED ART

Electrostatic discharge occurs when an object or person containing an excess of electrostatic charge comes into contact with another conducting object or person. As two bodies with differing voltages approach, the electric field increases with the inverse of the decreasing distance between them, until the dielectric breakdown of the intervening air is exceeded. At this point the air is transformed to a conducting plasma, allowing a sudden transfer of electrical charge between the bodies.

If the interaction occurs between a person and an electronic device, the inrush of current may damage any sensitive electronics present on the device. If the differential voltage is sufficient to generate an electric spark, it might ignite any proximate flammable or combustible substances. Companies involved in electronics development and all aspects of their supply chain must pay close attention to static charge mitigation in order to maintain product quality and reliability. In factories or warehouses where flammable or explosive chemicals are present, advancements in ESD mitigation stand to greatly improve workplace safety.

Conventional ESD mitigation products rely on a direct electrical connection between the user and Earth ground to carry away excess charge, such as by a tethered conducting wrist strap (e.g., U.S. Pat. Nos. 7,085,120 and 5,548,469) or grounding footwear and floormats. Alternatively, cleanroom installations with climate control or air ionizers can reduce the probability for electrostatic discharges by accelerating the natural dissipation of excess charge from bodies to the environment. These approaches are prohibitively expensive, lack reliability, or inhibit the mobility of the user to move between stations or within a large warehouse space. Other solutions aim to mitigate charge buildup by shooting ions toward the subject (e.g., U.S. Pat. No. 8,730,641), yet these approaches are limited to static objects and would be difficult to implement with a user that needs to move around. Placing the ion gun on the user can help (e.g., PCT Publication No. WO2019216129 and Chinese Patent No. 100356821), but still creates challenges of aiming the ion gun toward the user.

SUMMARY OF THE DISCLOSURE

The following presents a simplified summary relating to one or more aspects and/or embodiments disclosed herein. As such, the following summary should not be considered an extensive overview relating to all contemplated aspects and/or embodiments, nor should the following summary be regarded to identify key or critical elements relating to all contemplated aspects and/or embodiments or to delineate the scope associated with any particular aspect and/or embodiment. Accordingly, the following summary has the sole purpose to present certain concepts relating to one or more aspects and/or embodiments relating to the mechanisms disclosed herein in a simplified form to precede the detailed description presented below.

Some embodiments of the disclosure may be characterized as an electrostatic mitigation device without a direct grounding connection comprising a sensing section, a discharge section, and a controller. The sensing section can be physically attached to a user's body, although a direct conductive connection to the skin is not needed since the sensing section can detect field strength and thus close proximity can suffice. The discharge section can be conductively coupled via one or more electrodes to a user's body. The controller can be coupled to both the sensing section and the discharge section (e.g., in electrical communication with both sections), and configured to, when the sensing section detects an absolute electrostatic potential between the user's body and a surrounding environment and one or more objects within the surrounding environment exceeding a threshold, instruct the discharge section to emit positive or negative ions of equal polarity to the absolute electrostatic potential to remove charge from the user's body until the absolute electrostatic potential falls below the threshold.

Other embodiments of the disclosure may also be characterized as an electrostatic mitigation device without a direct grounding connection comprising a means to detect electrostatic potential, a means to discharge at least a portion of the electrostatic potential, and an electrode. The means to detect the electrostatic potential is configured to detect the electrostatic potential of the user's body, to which the electrostatic mitigation device is coupled, relative to an absolute electrostatic potential of nearby objects. The means to discharge at least a portion of the electrostatic potential of the user's body operates by expelling positive or negative ions to the surrounding environment (charge equal in polarity to the electrostatic charge on the user relative to the nearby objects). The electrode can be coupled between the user's body and the means to discharge.

Other embodiments of the disclosure can be characterized as a method of maintaining a body below an electrostatic potential without a grounding connection. The method can include sensing an electrostatic potential of the body relative to the surrounding atmosphere and surrounding objects. The method can further include identifying when the electrostatic potential of the body reaches a threshold. The method can further include generating a voltage between an ion gun and an electrode coupled to the body that is large enough to initiate ion discharge from the ion gun, the polarity of the discharge selected to reduce the electrostatic potential of the body relative to the surrounding atmosphere. The method can yet further include modifying the sensing after the ion discharge to reduce sensing artefacts caused by the ion discharge.

BRIEF DESCRIPTION OF THE DRAWINGS

Various objects and advantages and a more complete understanding of the present disclosure are apparent and more readily appreciated by referring to the following detailed description and to the appended claims when taken in conjunction with the accompanying drawings:

FIG. 12A illustrates an embodiment of the disclosure implemented as a sensing device separate from the ion discharge device;

FIG. 12B illustrates an embodiment of the disclosure implemented as a multiplicity of devices, each of which may be either a sensing device or an ion discharge device or a combination of both;

DETAILED DESCRIPTION

Figure 1:
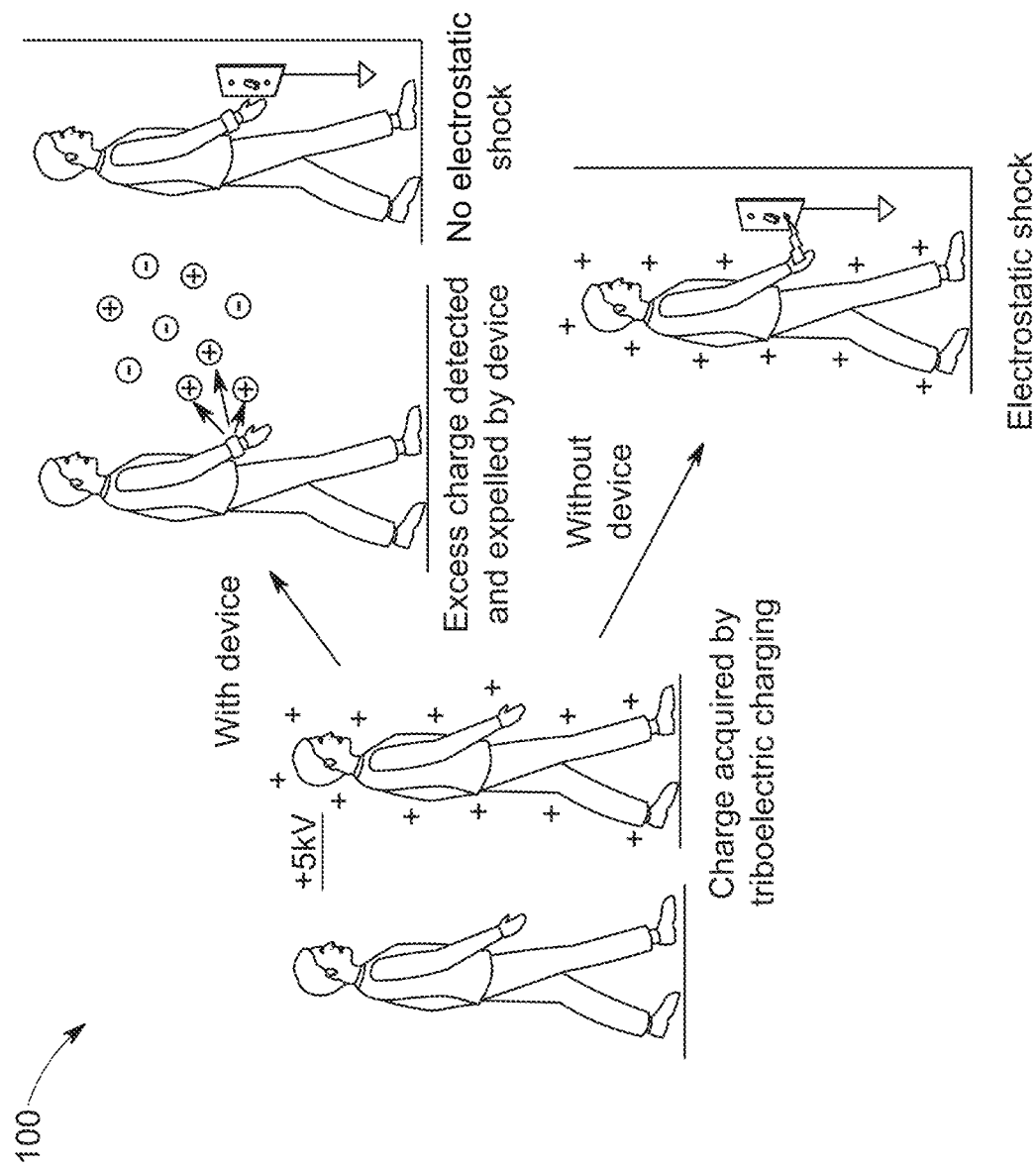
FIG. 1 is a standard use case of the electrostatic mitigation device.

The present disclosure relates generally to electrostatic discharge (ESD) mitigation, and more particularly, but without limitation, to systems, methods and apparatuses for a wearable ESD mitigation device that monitors charge and actively expels excess charge from the body via either positive or negative charged ions.

The word "exemplary" is used herein to mean "serving as an example, instance, or illustration." Any embodiment described herein as "exemplary" is not necessarily to be construed as preferred or advantageous over other embodiments.

Preliminary note: the flowcharts and block diagrams in the following Figures illustrate the architecture, functionality, and operation of possible implementations of systems, methods and computer program products according to various embodiments of the present disclosure. In this regard, some blocks in these flowcharts or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts, or combinations of special purpose hardware and computer instructions.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present disclosure.

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" or "under" other elements or features would then be oriented "above" the other elements or features. Thus, the exemplary terms "below" and "under" can encompass both an orientation of above and below. The device may be otherwise oriented (rotated 90 degrees or at other orientations) and the spatially relative descriptors used herein interpreted accordingly. In addition, it will also be understood that when a layer is referred to as being "between" two layers, it can be the only layer between the two layers, or one or more intervening layers may also be present.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items, and may be abbreviated as "/".

Embodiments of the disclosure are described herein with reference to cross-section illustrations that are schematic illustrations of idealized embodiments (and intermediate structures) of the disclosure. As such, variations from the shapes of the illustrations as a result, for example, of manufacturing techniques and/or tolerances, are to be expected. Thus, embodiments of the disclosure should not be construed as limited to the particular shapes of regions illustrated herein but are to include deviations in shapes that result, for example, from manufacturing. Accordingly, the regions illustrated in the figures are schematic in nature and their shapes are not intended to illustrate the actual shape of a region of a device and are not intended to limit the scope of the disclosure.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and/or the present specification and will not be interpreted in an idealized or overly formal sense unless expressly so defined herein.

The wireless anti-static device described herein allows for reliable and economical wireless prevention of electrostatic shocks, providing an increase in safety and productivity. Embodiments of the present disclosure feature a wireless anti-static device that can be worn by the user and prevents electrostatic discharge events. The battery powered device senses when the user accumulates excess electrostatic charge, positive or negative, and actively expels the excess charge away from the person where it is dispersed in the surrounding atmosphere. In some instances, two ion guns can be used—one to expel excess positive charge, and one to expel excess negative charge. An example system is described below. In other embodiments, different structures and/or techniques can be used to accomplish the same or similar results.

Wireless antistatic prevention is not a new idea but there has been no workable system devised until this disclosure. There are devices available commercially which are sold as a wireless antistatic solution, but are known to be ineffective to the point of fraudulence (see for example NASA's evaluation at https://sma.nasa.gov/news/articles/newsitem/2018/01/10/esd-wireless-wrist-straps-the-shocking-truth). These devices use so-called "passive ionization", which refers to the principle that a sharp point on a conductive surface may concentrate the charge on that surface sufficiently to cause some ionization and hence some removal of the charge. Testing of these devices by reputable laboratories against ANSI/ESD standards has shown that they do not work sufficiently well enough to replace grounded wrist straps, and their use has been banned in some organizations, including for example NASA. A recent review (see http://www.esdjournal.com/techpapr/sfowler/wireless.htm) by an industry expert concluded "It is our opinion that no currently available methods or devices exist which will effectively ground a person without a tethered cord to ground or at least a large capacitance. Sorry! Something that sounds too good to be true probably is."

Challenges for existing wearable ESD systems include the following:

Existing systems fail to wirelessly measure the potential of a human being, relative to their environment, with sufficient accuracy to allow one to reduce the potential of that person to within ANSI/ESD safety standards. When measuring human electrical potential (for example, in testing ESD devices for certification) a wired potential measurement is used. Typically, the subject holds one electrode of a voltmeter in their bare hand, and the other electrode is connected to a local (room) grounding point, and the voltmeter measures the potential difference between the two wired electrodes.

Existing methods also fail to wirelessly change the potential of a human body, without a conductive physical grounding connection or the firing of ions toward the human body.

This disclosure overcomes these challenges by introducing methods by which the potential of a human being relative to ground can be established wirelessly and to the extent that is necessary to meet ANSI/ESD standards. The methods of the disclosure suggest that a sufficiently accurate sensor, such as an electric field mill, be reduced in size by a factor of at least ten times smaller than previously achieved, and then be modified to be wearable. The present disclosure suggests that ion guns mounted on the body, and discharging into the surrounding environment rather than toward the user, can achieve the necessary control of the body potential. In other words, this disclosure takes the novel approach that potential control can be achieved by actively discharging ions from the body, rather than causing ions to be passively adsorbed by the body, or by draining charge off the body through a conductive path. Practically, this involved developing smaller ion guns and sensing circuits than is known in the art.

It is a consequence of the physics of electronics and ionic discharges that if the user wears both a potential sensor and an ion discharge device, there is considerable complication in avoiding detrimental interaction between these devices, particularly given that ion contamination is often the biggest source of error in non-contact potential sensors. In this disclosure, several novel methods of reducing this interaction are described.

One general use case for the wireless ESD prevention device is captured in FIG. 1. In this embodiment, the subject is a human being, and the device takes the shape of a wearable wristwatch. The user is shown to generate a large electrostatic potential via the triboelectric effect, for example by walking around on a carpeted surface. Without any ESD mitigation product or procedure in place, the subject may generate an electrostatic shock when touching a foreign object that is grounded or has sufficient electric capacitance. This object may be a grounded item such as a light switch or other apparatus, and the violent electrification of the air as the charge transfers from the subject to the object may ignite nearby flammable or explosive substances. In a separate scenario, the object that the charged subject comes in contact with may be a non-grounded piece of electrical equipment, and the resulting in rush of current may damage the device even if the charge on the subject or the capacitance of the object is insufficient to generate an electrostatic shock.

The herein disclosed wireless ESD prevention device senses that the user has obtained a charge (e.g., positive) that is above the preset threshold, and actively dissipates the excess charge from the subject to the surrounding environment by use of one or more ion guns. Therefore, the subject remains at an electrostatic potential equal or nearly equal to that of the nearby objects in its environment and can interact with these objects safely without instigating any damaging transfer of charge.

Figure 2:
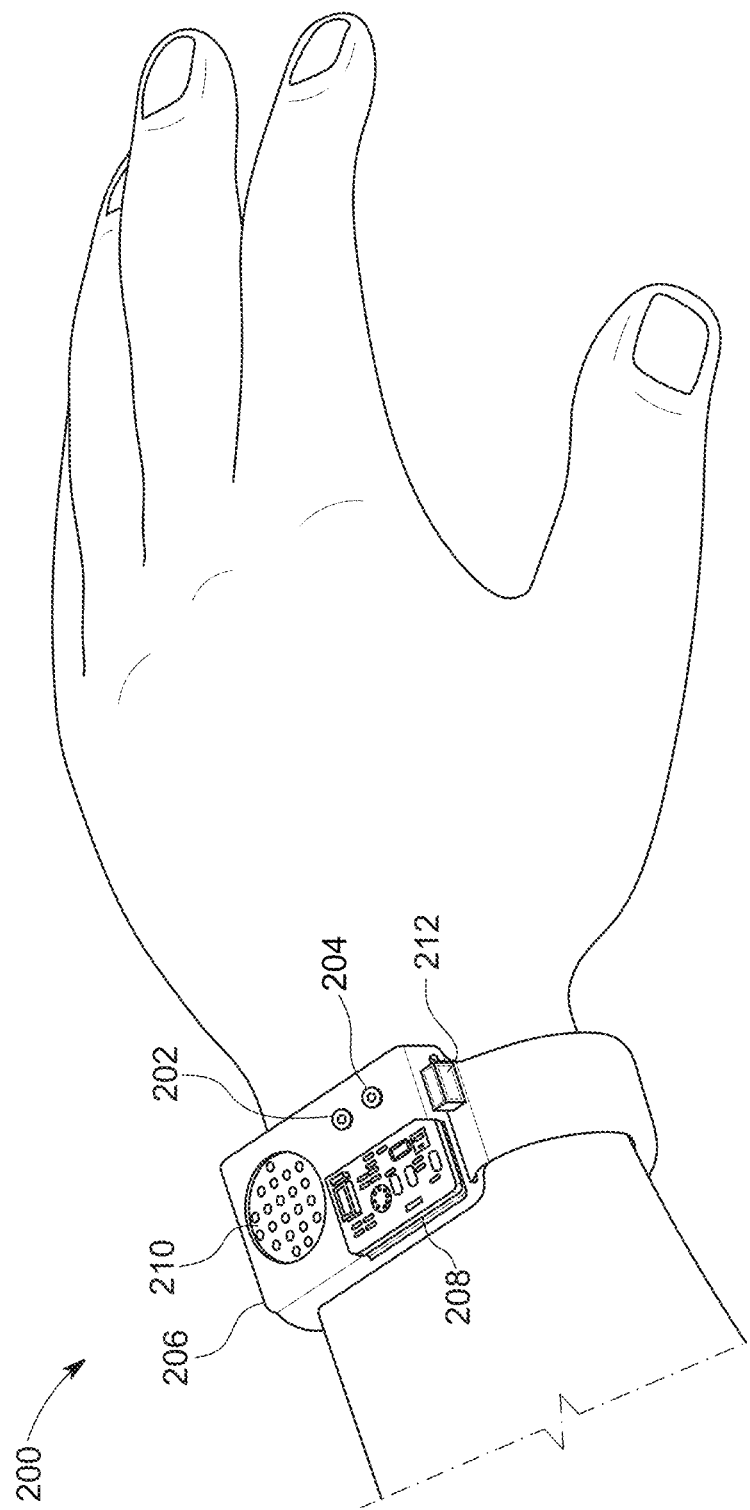
FIG. 2 is one possible embodiment of the electrostatic mitigation device as a wristwatch.

One embodiment of the disclosure is a wristwatch as shown in FIG. 2. The electrostatic mitigation device 200 may possess a button 202 to turn the device 200 on and off and change the operational mode, as well as indicator light emitting diodes (LEDs) 204 to provide feedback of measurement values and demonstrate successful discharge and charge mitigation operation of the device 200. The device 200 is autonomous, not requiring human interaction beyond the electrode connection for charge transfer from the user, and is no more physically incumbering than a typical smartwatch. An enclosure 206 ensures that the user is not able to physically interact with the internal circuitry 208 of the device (which is shown via a cutaway in the lower left of the enclosure 206), especially the high voltage components. However, there could be one or more physical perforations 210 in the enclosure 206 to allow the expelled ions to depart the device 200 and the subject, or to improve the sensing accuracy. If the ion gun(s) extends outside the enclosure 206, additional perforations may not be needed. A charging port 212 may be utilized to recharge the power supply, or an opening may be included in the enclosure to replace the power supply. The charging port 212 may also serve as a communications port for downloading data or uploading software or operational parameters to the device.

Preferably, the electrostatic mitigation device 200 makes good conductive contact with a patch of skin of the user, and the point or region of ion expulsion away from the user is unimpeded. A conductive gel or other conductive fluid may be arranged between the user's skin and the electrode to aid in conduction from the user to the device 200. Other embodiments of the disclosure may take the form of a device that is incorporated into garments such as clean room smocks, gloves, hats, or other protective equipment such as helmets, to name a few non-limiting examples. In circumstances where the workplace environment or clothing requirements make it practical or necessary, the connection between the device and the wearer's skin may be made by using a conventional conductive wrist strap; but the strap, rather than being tethered to the bench or other fixed object, is tethered by means of a short lead to the device disclosed here, to provide a conductive path between the skin and the device.

FIG. 2 represents one embodiment of an electrostatic mitigation device, as more generally described relative to FIGS. 3-6.

Figure 3:
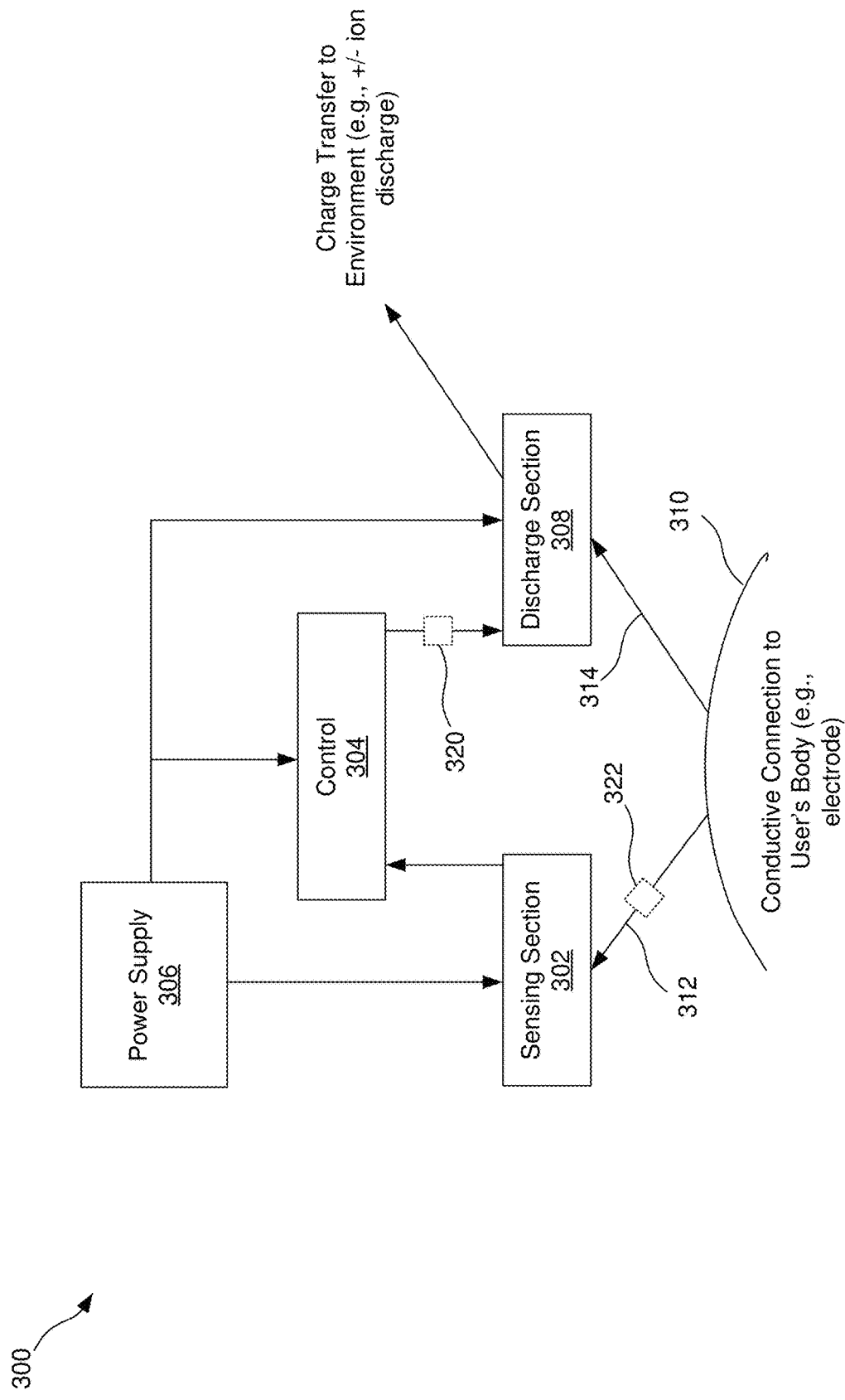
FIG. 3 illustrates an embodiment of components making up the electrostatic mitigation device.

More generally, the electrostatic mitigation device includes a conductive connection to the subject, a sensing section, a discharge section, a power supply, and a control. These are shown in FIG. 3. The device 300 can include a conductive connection to the subject 310, such as a conductive electrode that forms a conductive path for charge transfer between the subject and the device 300. In some embodiments, the conductive connection 310 can be implemented as multiple connections to the subject, especially where multiple sensing locations on the subject are used. A single sensing section 302 can be used in combination with a single sensing location or multiple sensing locations. The discharge section 308 can include a means for converting charge transferred through the conductive connection to the subject 310 into ions discharged into the surrounding environment. This can include one or more ion guns, such as one or more positive ion guns and one or more negative ion guns. The sensing section 302 and the discharge section 308 can include independent couplings 312, 314 to the conductive connection to the subject 310. In some embodiments, the couplings 312 and 314 can include two or more conductive paths.

A control section 304 can coordinate operation of the discharge section 308 based on measurements in the sensing section 302. For instance, the control section 304 may monitor for a first absolute charge threshold to be reached or surpassed, based on measurements of positive and negative charge by the sensing section 302. When this condition is met, the control section 304 can instruct the discharge section 308 to generate positive or negative ions of the opposite polarity to the charge build up, thereby decreasing the sensed charge buildup to below a second threshold. The second threshold can be equal to the first threshold or can be lower than the first threshold (i.e., where some hysteresis is desired to avoid instability in the control section 304). In other words, the sensing section 304 can either be configured to (1) instruct the discharge section 308 to discharge whenever the sensing section 302 measures an absolute charge buildup above a first threshold, or (2) instruct the discharge section 308 to discharge a certain amount of charge whenever the sensing section 302 measures an absolute charge buildup above the first threshold. The threshold may be stored in memory, for instance the memory 1106 in FIG. 11. One example of the control section 304 is the control processor 1104 and memory 1106 in FIG. 11. The control section 304 may also include a user interface, such as the user interface 1108 shown in FIG. 11.

A power supply 306 (e.g., a rechargeable battery) can provide power to the sensing section 302, the control section 304, and the discharge section 308.

Figure 4:
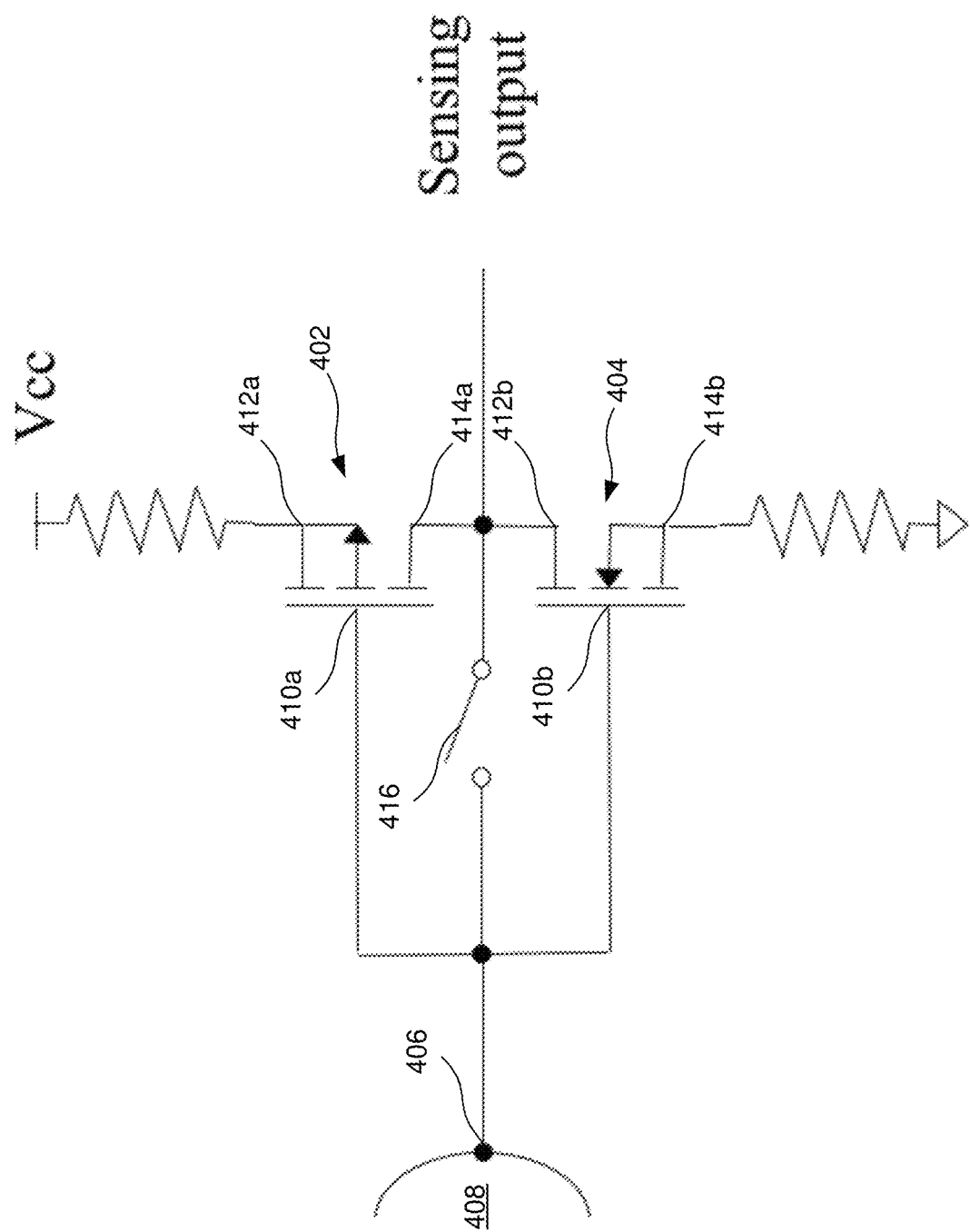
FIG. 4 illustrates an exemplar wearable sensor circuit for sensing the electric potential of the human body.
Figure 5:
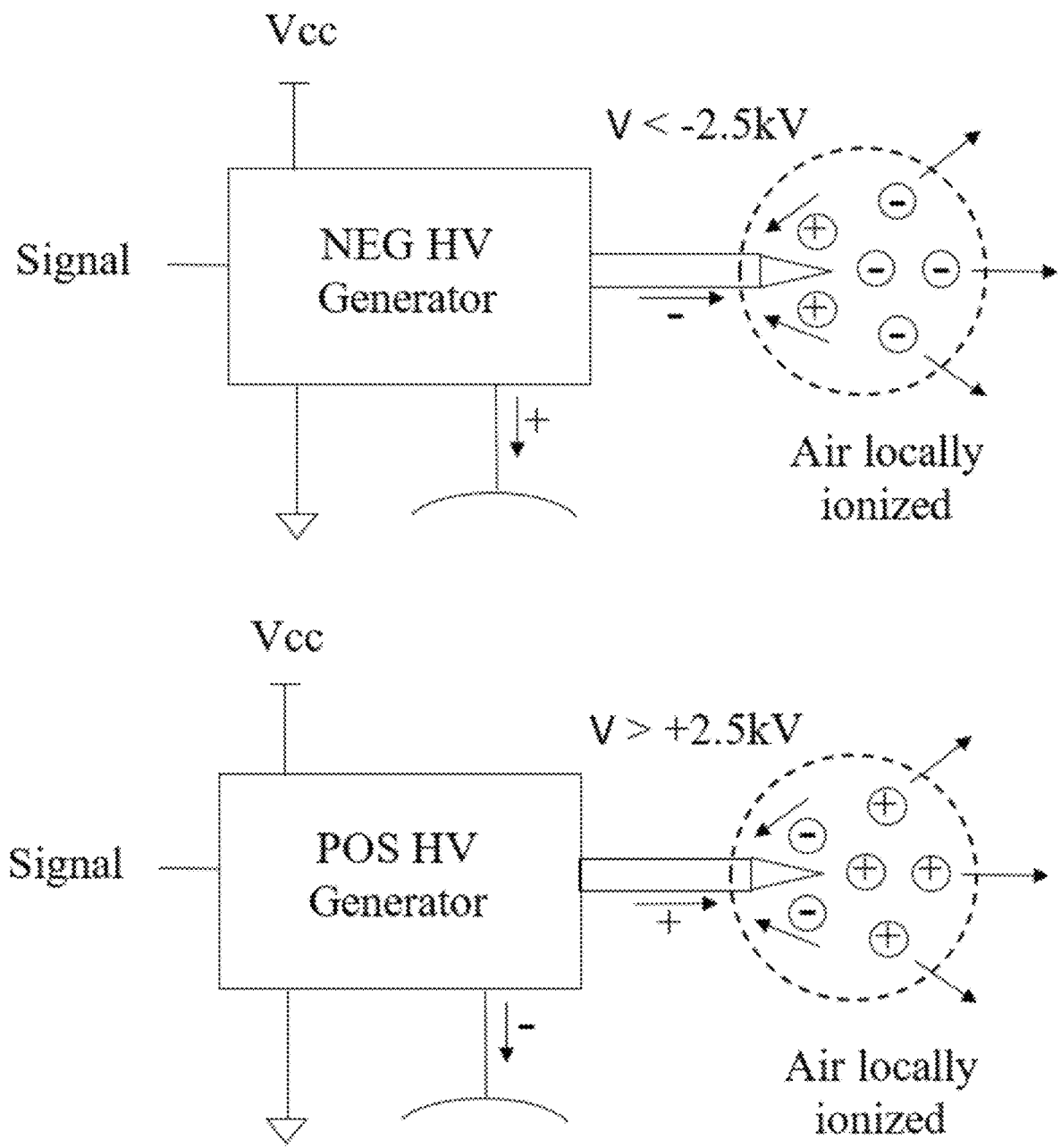
FIG. 5 illustrates an embodiment of operation of the negative and positive ion guns to remove charge from the subject.
Figure 6:
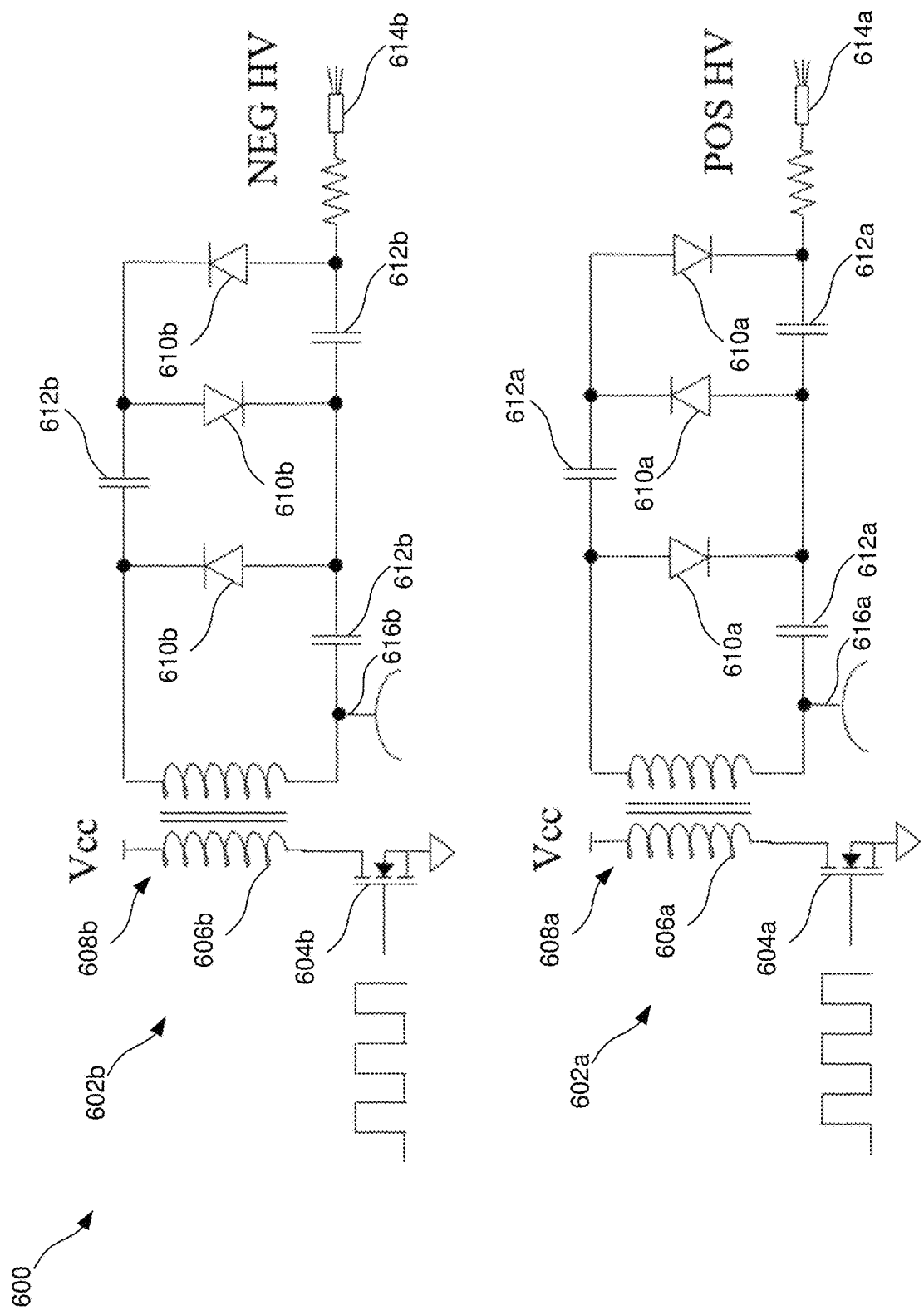
FIG. 6 illustrates a circuit topology for the positive and negative ion guns of FIG. 5.
Figure 7:
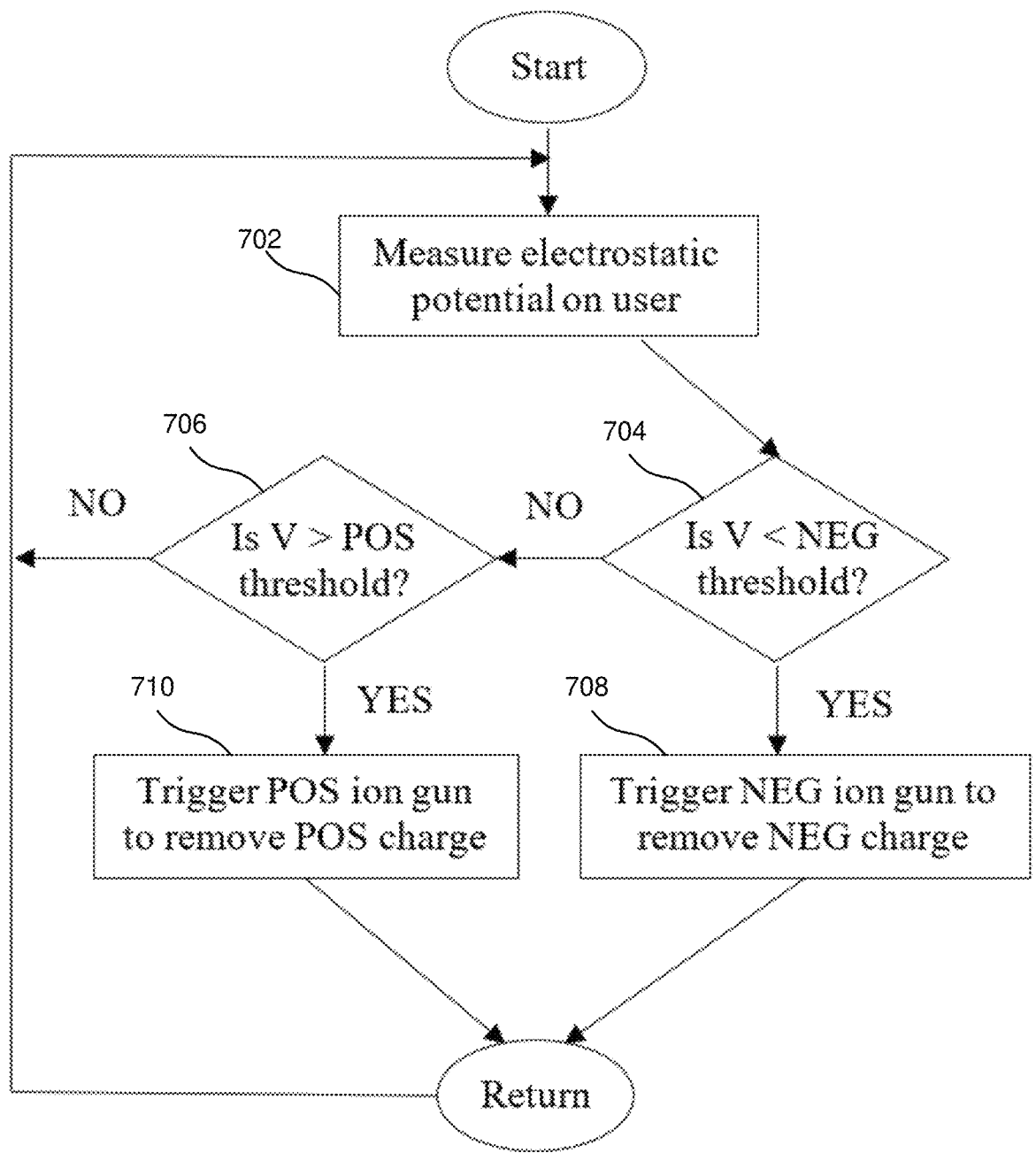
FIG. 7 illustrates an embodiment of a method of controlling the electrostatic mitigation device.

An illustrative sensing circuit is shown in FIG. 4, and exemplary discharge systems can be seen in FIGS. 5-7.

Sensing Section

Figure 11:
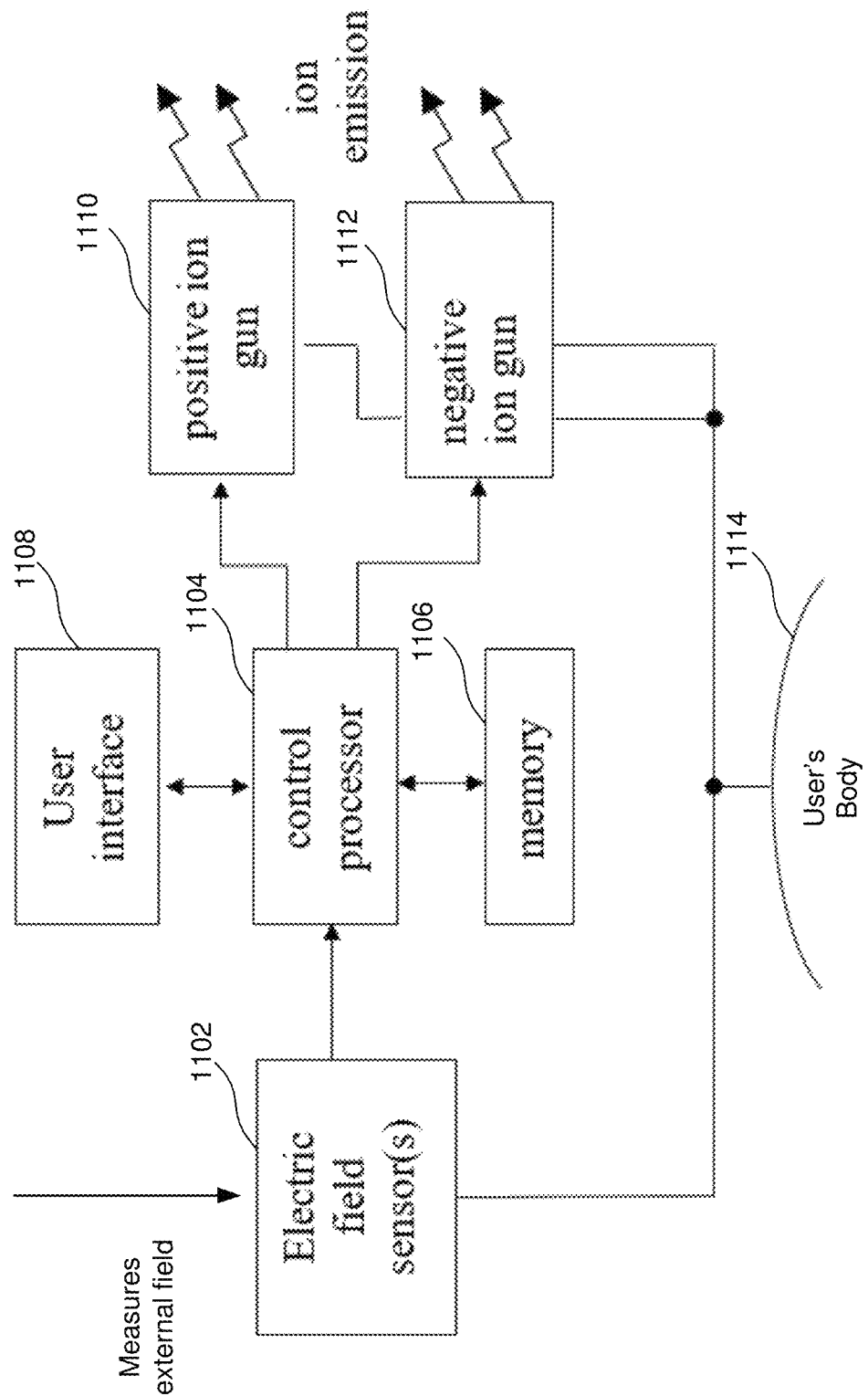
FIG. 11 shows an embodiment of an ESD mitigation device with positive and negative ion guns.

The sensing section 302 can use one or more electric field sensors, such as electric field sensor(s) 1102 in FIG. 11, in proximity or in contact with the user's body (e.g., 1114) and optionally distributed in a spaced apart fashion (e.g., see FIG. 12B). In some embodiments, the sensing section 302 uses a miniature electric field mill (EFM) (e.g., see FIG. 15). An EFM is a device in which a conductor is alternately exposed to the electric field to be measured and then shielded from it. More specifically, an EFM includes a spinning set of shutter blades that alternately cover and uncover an anode plate (the sensor electrode) that is alternately charged by the electric field when uncovered and the charge state determined followed by discharge of the anode plate when covered. Synonyms of an EFM include, generating voltmeter and generating electric-field meter. An EFM is a reliable and accurate device for sensing DC or steady-state electric fields without being affected by ionized air particles in the surrounding atmosphere. The EFM may be in proximity to the user's skin (e.g., coupled to an outside of a garment), but not in conductive communication with the user's skin, or may be in conductive communication with the user's skin.

Figure 15:
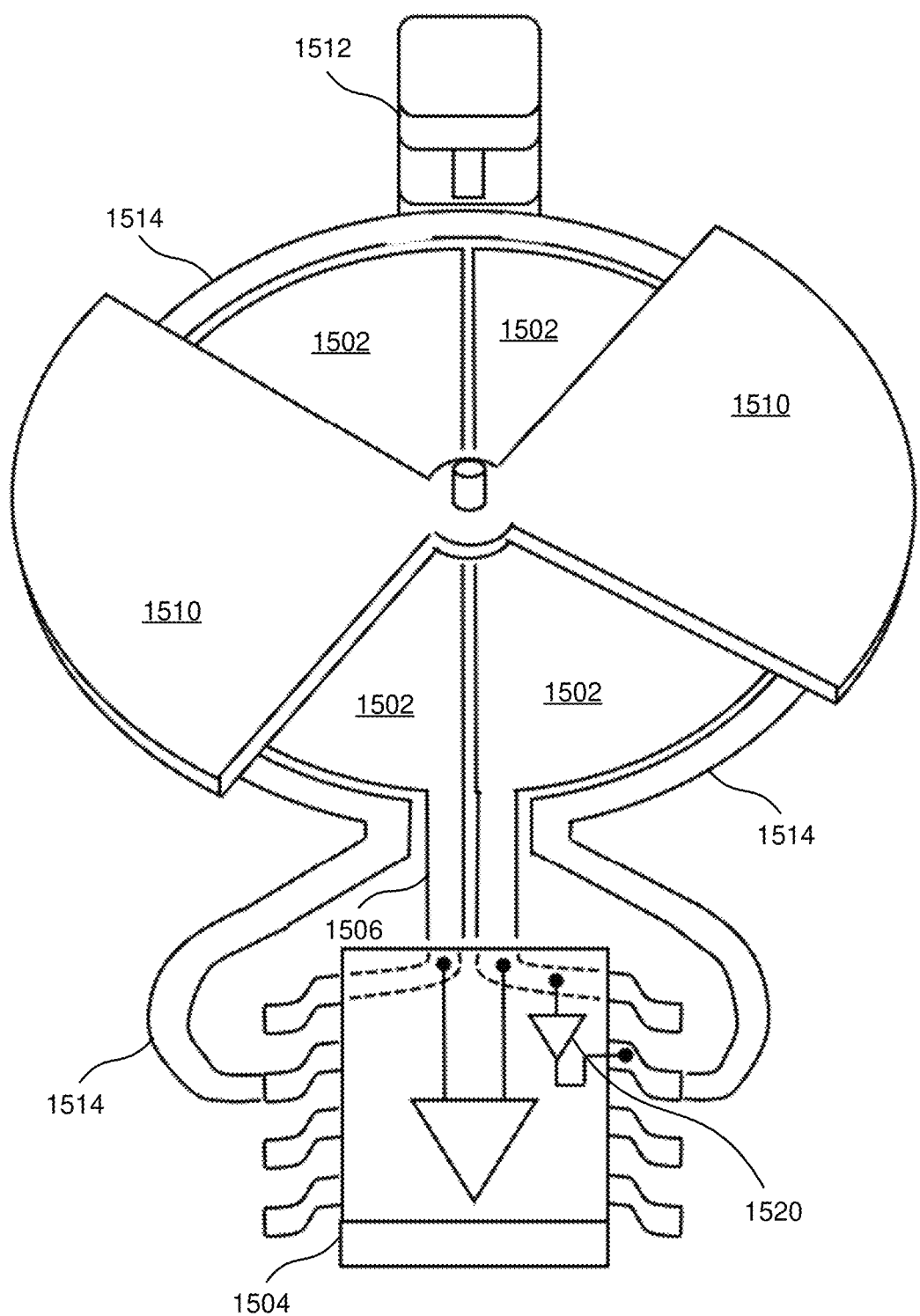
FIG. 15 shows an embodiment of a miniaturized electrical field mill.

A small electric field mill such as, but not limited to 12 mm×12 mm×12 mm in size, could be integrated into the sensing section 302 to act as the electric field sensor. FIG. 15 shows an embodiment of a miniaturized EFM, being roughly 12 mm×12 mm×12 mm in size. Those of skill in the art have been unable to develop such small EFMs in the past because the sensitivity of an EFM in measuring electric fields is proportional to the size of the conductive sensor (anode) plates and rotating shutter described above, and also to the rotational speed of the shutter. These two factors mitigate against wearability (because the size of prior EFMs is larger than a wearable form factor, and high rotational speed in the shutter requires high power consumption from the shutter motor drive). The EFM used in this disclosure has been successfully miniaturized by means of the following novel approaches:

1. The sensor electrodes 1502, rather than being fabricated from metal plate as is commonplace, are printed in copper coating (or another conductive film) on the same printed circuit board (PCB) that carries the electrode amplifier 1504. This allows for extremely small and precise electrode 1502 dimensions, and very short (approximately 1 mm) signal paths 1506 from the sense electrodes 1502 to the amplifier 1504, thereby reducing electrical noise. It also allows for the provision of an electronically driven shielding conductor 1514 to be arranged circumferentially around the sensor electrodes 1502, integrated into the same PCB. The shielding conductor 1514 may be actively driven by a buffer 1520 at the same potential as the inputs to the amplifier 1504, as is known to help prevent current leakage in sensitive electronics. This shielding conductor 1514 is driven to the same voltage as the sense electrodes 1502, which dramatically reduces charge leakage onto the sense electrodes 1502. These and other factors described below have significantly reduced the electrical and mechanical noise of the EFM sensor, thereby compensating for the lower sensitivity caused by smaller size.

2. The shutter 1510 is driven by a miniature electric motor (not visible), which is small enough to be integrated onto the same PCB that carries the sensing electrodes 1502 and amplifier 1504. This allows the motor case and the shutter 1510 also to be driven at the voltage of the sense electrodes 1502, thereby also reducing charge leakage artefacts on the sense electrodes 1502. It also has the effect that the entire EFM system is integrated into a single PCB, rather than being a multi-layer structure of metal electrodes, motor support plates, and shielding plates, and PCBs.

3. The sense electrode signal is electronically demodulated synchronously with the position of the shutter 1510. This is standard in many EFMs, but in all prior EFMs, the shutter position is measured by placing a second rotating toothed plate (sometimes called a "signal star") on the motor shaft, that rotates with the shutter and periodically interrupts the beam of a fixed photodetector. The photodetector signal thereby indicates the position of the motor shaft, and hence shutter, for the purposes of demodulation. In the current disclosure, the photodetector 1512 is placed on the single PCB in such a way that the shutter 1510 itself interrupts the photodetector 1512 beam. This has several benefits—the signal is more accurate as it is derived directly from the shutter 1510 and not from a signal star "proxy" for shutter 1510 position; there is no need for a signal star; and there is no need for a further structure to support the photodetector 1512. Once again, this allows the entire sensor to be integrated onto one extremely small PCB and hence allows greater miniaturization of the EFM than was possible in the prior art. The photodetector 1512 can take the form of an optical interrupter in some cases, for instance a slotted optical switch can be used.

4. Reducing the size of all these components allows the use of an extremely small (4 mm dia.×8 mm length, or less) electric motor to drive the shutter 1510, and this combination of a very small motor with very small shutter 1510 enables a very low power consumption in the device, so that it can operate for many hours from a battery that is small enough for a wrist-watch form factor and light enough to be attached to and hang from garments.

It should be appreciated that FIG. 15 represents just one structure for implementing a miniaturized EFM, and in other embodiments, different shapes, sizes, and orientations of the components, such as the sense electrodes 1502 and the shutters 1510 can be used.

EFMs are effective for measuring DC electric fields, but can also independently measure ionic current independently from a DC electric field. Thus, the inventors recognized that an EFM could be used in an embodiment of the electrostatic mitigation device 300 to measure both (1) an electric field for sensing charge buildup on the user and (2) an ionic current into the EFM for sensing artefacts (or errors or noise) of measurement caused by the ion gun(s) (mitigation of artefacts will be discussed in detail in a later section of the disclosure).

In some implementations the sensing section 302 can be embodied as a vibrating plate electric-field meter, shutter type electric-field meter, or cylindrical field mill, as discussed in U.S. Pat. No. 8,536,879, which is incorporated herein by reference. These devices determine the electric field by measuring modulated, capacitively induced charges or currents sensed by conducting electrodes. A vibrating plate electric-field meter (or vibrating probe) is a device in which a sensing plate is modulated below the aperture of a faceplate in the electric-field to be measured. Shutter-type electric-field mills are grounded and distort the electric-fields in their vicinity. Shutter type electric-field mills have a sensing electrode that is periodically exposed and shielded from the electric-field by a grounded rotating shutter. Cylindrical field mills measure the electric field by measuring the amplitude and phase of the current $i_c(t)$ flowing between two half-cylinder electrodes rotating with constant angular velocity $\omega$, and connected to each other by a low-impedance measuring circuit. An isolated cylindrical field mill can be a preferred version of a cylindrical field mill since these do not distort the electric field in their vicinity. Cylindrical field mills also measure ion currents along the space field lines terminating on them. With two orthogonally mounted sensors, it is possible to measure the 3-dimensional electric field, and a single sensor can measure the 2-dimensional field perpendicular to its axis of rotation. At the same time, an electric field mill includes moving parts, such as a high rpm motor (e.g., 1650 rpm) and two metallic coaxial disks separated by a fixed distance, and therefore may suffer from bulk, complexity, sensitivity to stress and wear, and may require frequent servicing.

To overcome these challenges, the sensing section 302 can alternatively be implemented as a shutterless sensing section. For instance, the sensing section 302 can be implemented as shown in FIG. 4, as a matched pair of switches, such as n-type 402 and p-type 404 metal-oxide-semiconductor field-effect transistors (MOSFET). This arrangement forms a voltage divider relative to the rail voltage, Vcc, such that the sensing output is half of the rail voltage, Vcc, when both switches 402, 404 are equally conducting (i.e., when there is a zero-net charge on the electrode 406). Each of the two switches 402, 404 are controlled via a conductive connection to the electrode 406. As a net negative charge accumulates on the user 408, the gates 410*a* and 410*b* of the MOSFETs 402, 404 obtain a lower voltage than the sources 412*a* and 412*b*, due to the inherent gate capacitance, and the p-type MOSFET 402 begins conducting more than the n-type MOSFET 404, therefore pulling the sensing output towards Vcc. When a net positive charge accumulates on the user 408, the n-type MOSFET 404 conducts more than the p-type MOSFET 402 and the sensing output is pulled towards ground. Thus, the absolute electrostatic potential of the user 408 to which the device 300 is connected can be accurately and quantitatively measured. Although FIG. 4 utilizes MOSFETs, other types of switches, such as JFETs and BJTs as two non-limiting examples, could also be used. Further, two or more of the circuit 400 shown in FIG. 4 could be implemented where multiple electrodes 406 contact the subject 408 at different locations on the subject 408 (e.g., see FIG. 12). As compared to typical field sensors, such as shutter type field mills, this shutterless sensing section 400 achieves absolute electrostatic potential measurements without moving parts, and is a compact, low cost and low power circuit. However, this type of circuit is prone to errors resulting from drift of the system relative to some external absolute potential, and also ionic contamination of the electrode 406, and may require a periodic rest to neutralize these effects. This reset is implemented by momentarily closing the switch 416.

In another embodiment, the sensing section 302 can use an "absolute voltmeter," which measures the potential of a body without reference to an external voltage. Such a sensor could help maintain independence from ionic currents. Absolute voltmeters, while having been patented and constructed in the laboratory, have not been commercially produced or utilized and may not be miniaturizable to the extent preferred for wearability. EFMs are currently regarded as the gold standard for electric field and non-contact electric potential measurement, but their moving parts constitute a reliability issue. Solid-state sensors such as that illustrated in FIG. 4 are cheap, simple, and low power, but are affected by drift and contamination to an extent that may render them insufficiently accurate in this application.

It is important to remember that the user's body is likely an electrical conductor, and external electric fields can generate local differential charge distributions within the body. Therefore, the location of the sensing circuit may be influenced by nearby charged objects. This type of situation—when there are charged objects in the vicinity, as well as the body having some non-zero charge—is difficult from an ESD mitigation perspective, as there is no ideal solution to prevent ESD (as there is when the environment is uncharged, and all that is required is to eliminate the charge on the body). In practice, the automatic action of the disclosed device will be to equalize the body to the same potential as the most proximate charged body. Considering the overall operation of the device, this will have the effect of equalizing the electrostatic potential of the subject to the potential of the nearby object(s), therefore still preventing electrostatic discharge when contact is made to this object. This is in most scenarios the optimal outcome for the situation, as it prevents the wearer from generating a spark or ESD event when in local contact with objects. In other embodiments, the coupling 312 can couple to multiple locations on the user's body or garments or can be distributed across multiple couplings 312 (e.g., see FIG. 12). Either way, in operation the coupling(s) 312 enables the sensing section 302 to determine an averaged electrostatic potential relative to the surrounding environment and/or relative to an absolute electrostatic potential of surrounding objects. In some embodiments, the sensing section 302 is merely coupled to the user and not necessarily through a conducting path since only field measurements are made. The control section 304 can seek to equalize the user's electrostatic potential to (1) the averaged electrostatic potential relative to the surrounding environment as well as relative to an absolute electrostatic potential of surrounding objects, (2) the averaged electrostatic potential relative to the surrounding environment, or (3) an absolute electrostatic potential of surrounding objects. As introduced above, scenarios where there are charged objects in the environment present a challenge in terms of which potential to force on the wearer's body, in order to minimize ESD damage. As mentioned, operating to minimize ESD events is likely the optimal approach, and this might involve adjusting the body potential to be the same as that of the nearest object, rather than that of the surrounding environment. Depending on the operational situation, the best outcome might entail any one of approaches (1)-(3) above. It would also likely be advantageous if the device were to issue an audible, visible or electronic alarm when it detects local charged objects, as (in an electronics manufacturing facility for example) this represents a failure of other components of the facility's ESD management system. This operation could, for example, be implemented by placing a multiplicity of EFMs or other means of sensing at different points on the body, such as on both wrists and either on the head or shoulders, or both (e.g., see FIGS. 12A and 12B). This might be useful when the fields surrounding the subject are sufficiently inhomogeneous that a single field measurement from a single point on the subject's body does not provide a sufficiently accurate electrostatic potential with respect to local objects. In this case, the device 300 would benefit from adequate computing power to calculate the correct neutral potential from the multiple sensing measurements, and to control the discharge section 308 accordingly.

Discharge Section

In some embodiments, the discharge section 308 can include a negative and positive polarity ion gun, as depicted for instance in FIGS. 5 and 11. It is commonplace in the control of ESD to use fixed mounted ion guns (on the ceiling of a manufacturing facility, for example) to generate an abundance of ions in the room's atmosphere to be absorbed by user's moving through the ionized space and thereby neutralize statically electric charge on those users. It has been suggested (e.g., see WO2019216129) that the ions can be directed at a person in order to reduce the charge on that person by absorption of ions. In this disclosure, a novel approach is taken that the ion guns are directly conductively connected to the body, and generate ions in the air (not aimed at the user) from ions removed from the body. The commonplace method described reduces the charge on the body by producing ions in the air, which are then absorbed by the body. The disclosed methods work by removing charge from the body to produce ions in the air, which then drift away or are absorbed by nearby conducting structures. A collateral benefit of the disclosed methods is that, because the body charge is directly and actively removed from the body, rather than haphazardly dissipated by the absorption of airborne ions, the voltage of the body is actively controlled, and can be driven to zero voltage with confidence, at a known and predetermined rate.

The ion guns (e.g., 1110 and 1112) use a driver circuit or generator to provide a sufficiently high voltage to a sharp geometry such as a needle or a carbon fiber brush with multiple sharp points. Charge buildup at this sharp geometry eventually exceeds a first absolute charge threshold that causes dielectric breakdown of the surrounding air. Charge carriers present in the air of the same polarity of the sharp geometry are repelled, while those of opposite polarity are drawn to the sharp conducting point. In this manner, charge transfer is enabled between the surrounding air and the subject to which the electrostatic mitigation device is connected. The first absolute charge threshold voltage can be determined by the discharge geometry and the conditions of the surrounding air (such as moisture content), but at higher voltages, the kinetic energy of the repelled particles is increased, thus increasing the efficacy of the ion gun(s).

FIG. 11 shows an alternative to FIG. 3, where the discharge component of FIG. 3 is replaced with two ion guns, and the sensing component of FIG. 3 is replaced with one or more electric field sensors. The ion guns 1110, 1112 can include a positive ion gun 1110 and a negative ion gun 1112, an appropriate one used to transfer charge to the surrounding air, or transfer charge from the surrounding air to the user's body 1106, based on sensed charge build up on the user's body 1106 (and optionally also based on charge buildup sensed through external fields at the electric field sensor(s) 1108). In some embodiments, the two ion guns 1110, 1112 can include distinct power sources (not shown), while in others, a single power source can drive both ion guns 1110, 1112. Where a single power source is used, a switch or other subsystem, can be used to direct the power to one of the two ion guns 1110, 1112.

FIG. 6 shows one embodiment of a discharge circuit that can be used in the discharge section 308. The discharge circuit includes a positive ion gun 602a and a negative ion gun 602b. A pulse width modulated (PWM) signal is supplied to the gate of a transistor 604a, 604b in series with a low inductance winding 606a, 606b of a high turns ratio transformer 608a, 608b (e.g., primary side). This generates a high voltage with alternating current on the high inductance side 606a, 606b of the transformer 608a, 608b (e.g., secondary side). The illustrated collection of high voltage diodes 610a, 610b and capacitors 612a, 612b forms a Cockroft-Walton voltage multiplier that also rectifies the signal, producing a high voltage at the discharge electrode 614a, 614b relative to the subject electrode 616a, 616b (coupled to the user). The polarity of this voltage is determined by the orientation of the diodes 610a, 610b. The terminal high voltage obtained is a function of the input voltage, the pulse width modulation, the transformer 608a, 608b ratio and the number of stages in the voltage multiplier; these may be specified to produce an appropriate voltage, for instance, in the range 2.0-4.0 kV. Too low a voltage may produce insufficient ion flux, whereas too high a voltage may prove difficult to accommodate in terms of shock or flashover hazard. Many other topologies may be utilized to generate the high voltage necessary for the ion guns, including some designs using only a single transformer for both positive and negative ion guns. Although FIG. 6 shows two distinct circuits/ion guns, one for positive and one for negative discharge, in other embodiments, the diodes could be replaced by switches such that a single circuit could be used to provide both positive and negative discharges.

It is also possible to generate high voltages, using piezoelectric transformers. For instance, the discharge section 308, and the ion guns in FIGS. 5 and 5 as well as the ion guns 1110 and 1112 in FIG. 11, could be implemented using piezoelectric transformers. Such transformers are electromechanical devices and may also produce airflow as a secondary effect; these devices are called electrohydrodynamic pumps. As noted below, airflow may increase the efficiency of the ion guns used in this disclosure, and therefore piezoelectric generation of the ion gun voltages may be advantageous in this disclosure, as it may be possible to generate the high voltages and airflow from a single circuit device.

Control Section

Lastly, a control section can process the electrostatic sensing signal and send control signals to the appropriate ion gun to remove the excess charge from the subject. In an embodiment, the control architecture can be implemented as a bang-bang control algorithm, as depicted in FIG. 7. The method 700 can include measuring an electrostatic potential of a user at one or more points relative to the surrounding environment and/or relative to an absolute electrostatic potential of surrounding objects (Block 702). The potential is then compared to a negative threshold, and if the measured potential is more negative than the negative threshold (Decision 704=yes), then the method 700 instructs the negative ion gun (e.g., 602b) to discharge negative ions (Block 708), thereby removing negative charge from the subject. If the measured potential is not less than the negative threshold (Decision 704=no), then the method compares the measured potential to a positive threshold in Decision 706. If the measured potential is not less than the positive threshold (Decision 706=no), then the method 700 moves to a next measurement (returns to Block 704). If the measured potential is less than the positive threshold (Decision 706=yes), the method instructs the positive ion gun (e.g., 602a) to discharge positive ions (Block 710), thereby removing positive charge from the subject. After either discharge (Blocks 710, 708), the method 700 returns to take another potential measurement (Block 702).

In other embodiments, more complex control systems may be utilized and tuned for the specific subject and environment, such as, but not limited to, proportional-integral-derivative (PID) control algorithms or nonlinear control algorithms.

In some instances, it may be desirable to store information regarding the sensed electrostatic potential of the user and electrostatic discharge operations for further analysis. This information may be stored in a local memory chip within the device for later upload and analysis, or it may be streamed from the device wirelessly for real time monitoring. This data may be used to gain knowledge about the geospatial likelihood of acquiring electrostatic charge within an environment, or to monitor the likelihood of user practices in generating dangerous electrostatic charge, or to generate alarm signals in an ESD management system. Moreover, successful operation of the device can be monitored to ensure compliance with ESD mitigation protocols.

Mitigating Artefacts and Other Unwanted Influences on Sensing

It is not unexpected that a high voltage ion discharge, in close proximity to sensitive sensor electronics, will produce noise, errors, or artefacts in the sensing signal. The noise or artefacts may arise from a number of sources:

1. Electromagnetic interference (EMI) between the high voltage discharge components and the sensing circuits.
2. Fluctuations in voltage supply caused by the high currents required for the high voltage circuits.
3. Ionic currents circulating from the ion guns to the sensor electronics.
4. Circuit noise caused by electric-field-induced charge movement in conductors of the electronics system.
5. Electric fields generated by ionic charge adsorbed onto the insulating surface of the device enclosure, or by the dielectric or electret nature of the material of the device enclosure.

Additionally, the effectiveness of the ion guns in emitting ions may be affected by the physical accommodation of the ion-emitting electrodes. Generally, these electrodes have one or a multiplicity of sharp points, which are designed to create a high electric field. However, the magnitude and shape of the electric field is also affected by the surrounding electrical potentials (such as may be created by local conductors, or by charged insulators in close proximity). Therefore, the geometry and material of the ion gun enclosure is considered in terms of its effect on the ion gun performance. It is also the case that the ions emitted by the ion gun adsorb or contaminate local surfaces, thereby affecting the ion gun performance, so there are cyclical or feedback effects to consider.

There are several methods for mitigating these problems, which may include circuit modifications; modifications to the mechanical and electrical structure of the device enclosure; methods of driving the ion guns in such a way as to reduce the magnitude of noise, errors, and/or artefacts; and physically separating the sensing elements from the ion discharge elements, by, for example, using an elongated housing, or two separate housings placed on different parts of the wearer's body, or a multiplicity of separate sensors and ion discharge elements on different parts of the body.

In some instances, a programmed microcontroller may be utilized to perform the control system tasks (e.g., the functions of control 304 and the method 700). In others, simple electronic circuitry may be utilized (e.g., discharge may be triggered via analogue circuits coupled to the sensing circuit). In some instances, the control system may implement time delays, of the order of some milliseconds, between reading the sensing signal and running the discharge system, and vice versa, in order to circumvent any interference between the two systems caused by the high voltage operation of the ion guns.

Figure 8A:
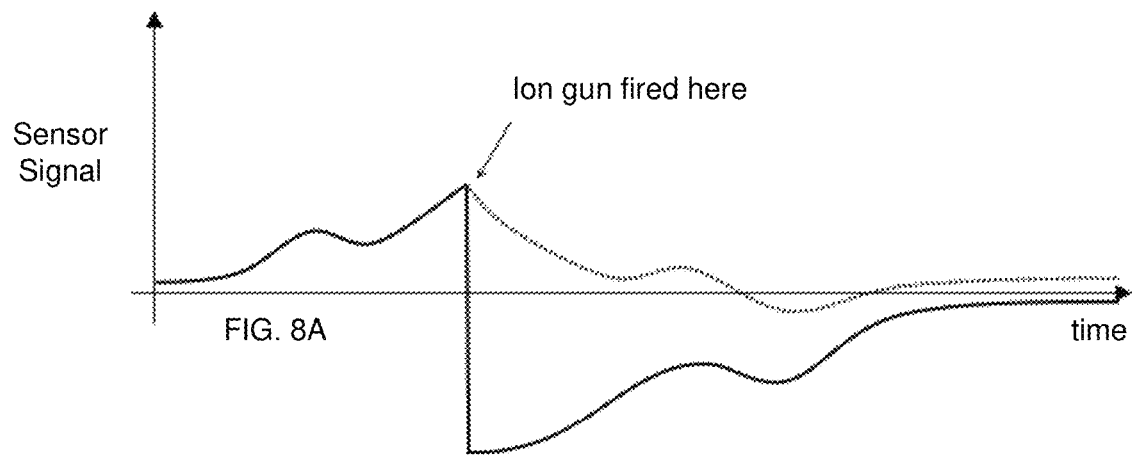
FIG. 8A illustrates a plot of the sensor signal as a function of time when the ion gun is fired.
Figure 8B:
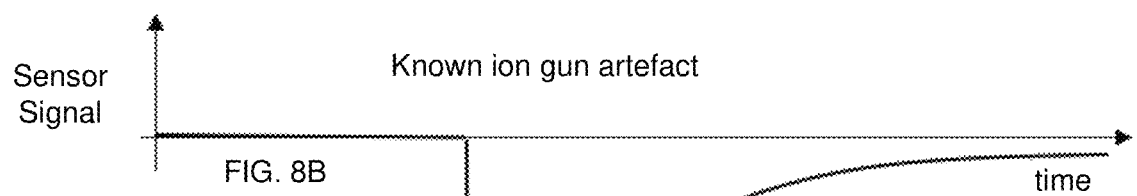
FIG. 8B illustrates a plot of a known artefact caused by ion gun discharge that forms a part of the plot in FIG. 8A.
Figure 8C:
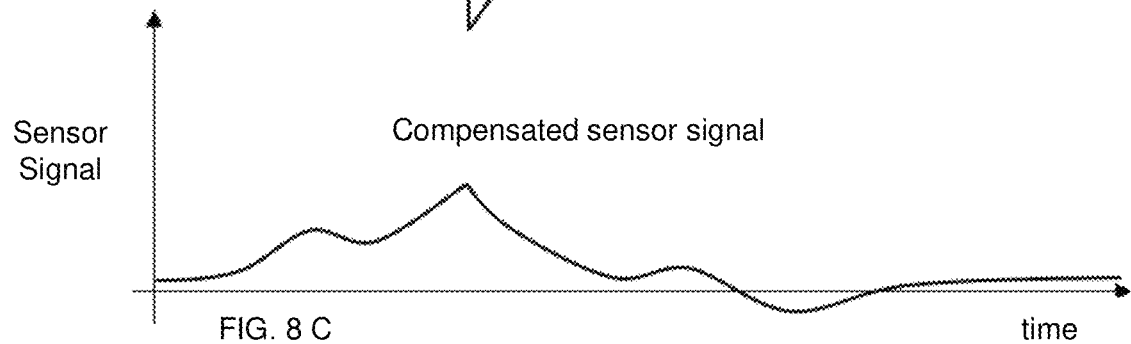
FIG. 8C illustrates a plot of the sensor signal as a function of time when compensation for the known artefact is used.

A more sophisticated control system may compensate for sensing noise, errors, and/or artefacts caused by the ion gun discharge. For example, it may be that the discharge causes an error spike in the sensor signal, which might decay exponentially or otherwise in time as is commonplace in electronics, as shown in FIG. 8A. If this effect is known, it is possible for the control system, upon an ion gun discharge, to subtract from the sensor signal the known error produced (see FIG. 8B), and calculate a corrected signal for some interval of time following the discharge (see FIG. 8C). The known error can be a sensed artefact compensation signal previously recorded. In FIG. 8A an exemplary sensor signal is shown including a negative spike resulting from the ion gun discharge. A signal for a similar known artefact is shown in FIG. 8B, and the corrected signal is shown in FIG. 8C (e.g., by subtraction of FIG. 8B). Another implementation could hold the control circuitry in a current (fixed) state for a period of time after any discharge, thereby using a less tailored, but less complex approach to false positives following discharges. Further, a sensor such as the electric field mill (EFM), which is capable of measuring both electric field and ionic current independently, may use those two variables in an algorithm to reduce the measurement noise, errors, and/or artefacts due to ionic currents. For example, the sensor artefact shown in FIG. 8B may be created by the ionic current impinging on the sensor. By measuring this current at the sensor, the exact shape of the curve in FIG. 8B could be established in real time, rather than recorded in advance or otherwise as described above. This would enable a more accurate elimination of this artifact from the sensor signal.

Figure 9:
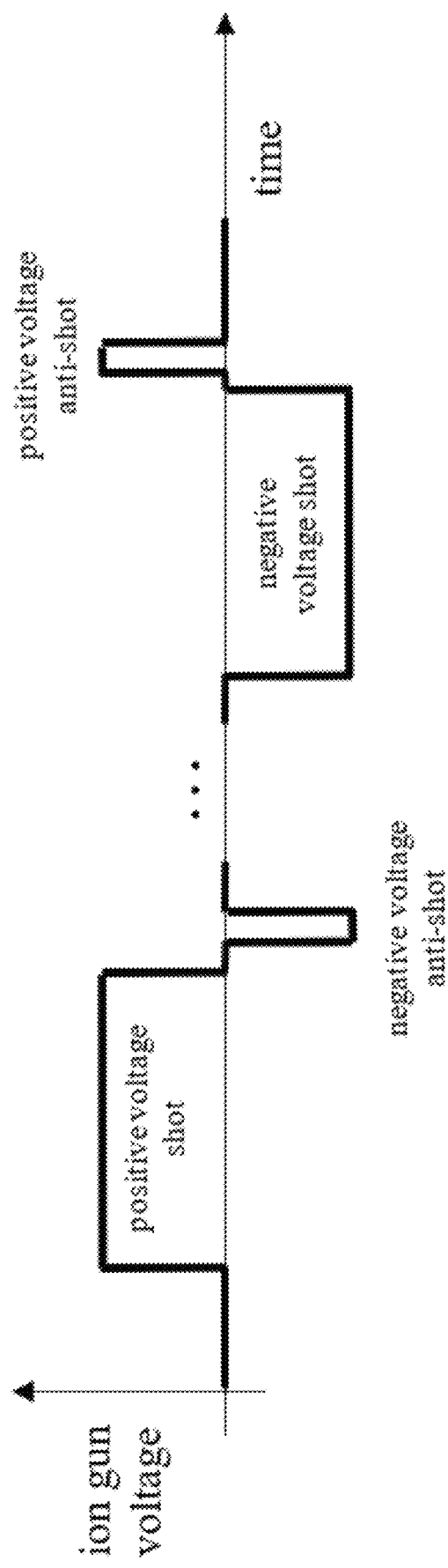
FIG. 9 illustrates a plot of positive and negative pulse "shots" quickly followed by short "anti-shots" to reduce artefacts in sensing caused by ion gun discharge.

Another method of reducing a number of types of unwanted effects of ion gun discharge, is to follow an ion gun discharge by a smaller discharge of the opposite polarity. This is shown in FIG. 9, where the initial discharge is referred to as the "shot", and the compensating opposite discharge is referred to as the "anti-shot". FIG. 9 shows first the combination of a positive shot with a negative compensating anti-shot, followed at some future time (indicated by an ellipsis) by a positive shot with a negative anti-shot. This approach can be effective since artefacts (e.g., those caused by adsorbed charge on insulated surfaces of the system) do not accumulate linearly in time as the discharge proceeds, but are predominantly caused by the initial moments of discharge. As such, a short anti-shot reduces most of the harmful effect of the shot while not substantially reducing the desirable magnitude of ion discharge generated by the shot. By "short" it is meant that each primary positive discharge pulse or primary negative discharge pulse is followed with an opposite polarity anti-shot pulse having a duration of less than 20% of, or 5-20% of, or 10-20% of, the primary positive/negative discharge pulse, so that the primary positive discharge pulse or primary negative discharge pulse maintains sufficient charge transfer to be meaningful (i.e., to substantially equalize electrostatic charge between the user and surrounding atmosphere and/or nearby objects). Although FIG. 9 shows positive and negative voltage changes as square waves, in other embodiments, one or both of the positive and negative voltage changes can have other than a square waveform. For instance, ramping, curved, or pulsing waveforms, to name three non-limiting examples, could be implemented.

In order to prevent interference in the system from ionized air particles present naturally in the environment or from the discharge of the ion guns, various forms of shielding may be implemented around some or all of the electric circuitry in the system. This shielding may consist of airtight enclosures, plastic potting of the electronics, or conducting boxes, also known as Faraday cages, that block electric fields from reaching the circuitry. For instance, two or more electrostatic shields may be used, and resistive links can be formed therebetween, the shields configured to reduce conduction between the two or more electrostatic shields.

To prevent or moderate the effects of surface charging as mentioned above, it is possible to manipulate the conductivity of the surface of the device enclosure. In an embodiment, a conductive coating on portions of the interior or the exterior of the enclosure (e.g., 206) can be provided, so that the adsorption of ions is mitigated by conducting these ions elsewhere, or so that the electric field in that area of the enclosure can be manipulated by specifying, through the use of electrical circuitry, the potential on that conducting portion of the enclosure. Various conductive areas of the enclosure can be connected electrically by means of conductors of specific resistance, allowing control of the conduction of charge from one area to another. It is also possible to connect these conductive areas of the enclosure to each other, or to the main electronic system, by means of switches (such as, for example, field effect transistor switches). This would allow, for example, for an area of the enclosure to be connected in one way during discharge events, and in another way during sensing periods. So, for example, an area could be electrically isolated from the main circuit during discharge events, in order to prevent that area from acting as an electrical sink for ions; but it could then be connected (shorted) to the main circuit during sensing events, to provide a fixed and known potential relative to the sensing circuit. As an example, FIG. 3 includes two optional switches 320 and 322 that can be opened during discharge and closed during sensing. In some cases, only optional switch 322 can be implemented, and again it can be opened during discharge and closed during sensing. In other embodiments, the optional switches 320 and 322 can be implemented as variable-resistance components and operated to provide partial isolation of the sensing section 302 from the conductive connection to the subject 310 when the discharge section 308 discharges ions. A controller can be configured to control the optional switches 320 and 322 or variable-resistance components to provide partial or full isolation of the sensing section 302 when the discharge section 308 is discharging ions.

In providing the material and coating for areas of the device enclosure, it is possible to control both the conductivity and surface adsorption of these areas. This allows for manipulation of both the local electric field, and the local adsorption of ions, in order to achieve the best performance of the system. For example, it might be appropriate to coat the exterior surface of the enclosure that surrounds the electric field sensor with a conductive layer, which could be connected to a fixed potential within the circuit, to provide a fixed plane of known potential as a reference for the sensor.

Similarly, it might be appropriate to coat the areas of the enclosure closest to the ion gun emitters with a layer which is both highly insulating and also impervious to ion embedding or adsorption, to prevent the buildup of a layer of charge close to the ion emitters which could affect their performance.

It is also possible to direct the passage of the emitted ions, using physical barriers in the form of internal or external baffles, channels, or other guide structures, so as to direct the ions away from the device and specifically away from the sensor(s) and associated electronics. One possibility for directing the movement of ions, which may also increase the discharge rate of the ion gun itself, is to place a source of forced air (such as a small fan) in the housing, with air ducting so that the air from the fan is driven past the ion emitter point in the direction in which the ions should preferentially move. This has the effect of blowing the ions (which are physical particles susceptible to forcing and being forced by an air stream) away from the device, thereby improving the discharge and reducing the interference between the ion guns and the potential sensor. It is also possible to create a so-called "ionic wind" air stream using carefully positioned electrodes to move the ions in a desired direction; the ions will entrain air in a flow, and this wind then serves to carry the ions further away.

It is also possible to accelerate ions in a particular direction by means of a conductive grid or similar electrode which is electrically driven at a different potential than the ions, and by this means to direct the ions in a desired direction. Piezoelectric high voltage transformers can also be used to create ions and direct them in a wind stream via a combination of physical movement and electromagnetic acceleration (sometimes referred to as electrohydrodynamic action). These devices may be suitable for use as the ion discharge component of this disclosure (e.g., 308).

Another arrangement to reduce interference between the ion gun discharges and the sensor is to physically separate the discharge section and the sensing section. This can be achieved by placing them apart in a larger sensor housing, or by placing the ion guns in a separate housing from the sensor, and placing these two housings at different points on the user's body. For example, the sensor could be placed on a wrist, and the ion guns on a shoulder or opposite wrist. As well as improving the sensing performance, this offers the possibility that the two parts of the device can be placed at a point where that part has more optimal performance. For example, it might be found that the sensor is most optimal when placed on top of the head (giving it an unrestricted overhead view of the surrounding environment), but the ion guns are more optimal when placed on the shoulder. It also allows for the possibility of a multiplicity of sensors and/or ion guns at various places on the body, in order to obtain more accurate sensing. The placing of sensors and discharge elements may also be determined by ergonomic and safety concerns. For example, for workers who have to place their hands inside an electronic structure such as a satellite bus while working, ion gun and sensor placements on the shoulders may be more ergonomic and safer than on the wrist. It may also be desirable to place the discharge elements so that the ion stream is not directed towards the electronics on which the worker is working (e.g., the discharge section may be placed on a user's back or rear of the waist or shoulders).

Figure 10A:
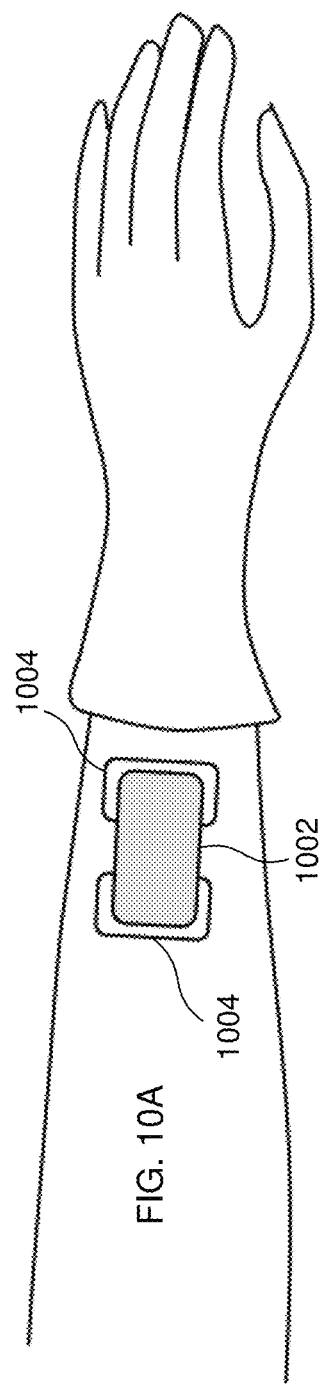
FIG. 10A shows the sleeve of a smock provided with an alignment bracket and one aperture through to the skin.
Figure 10B:
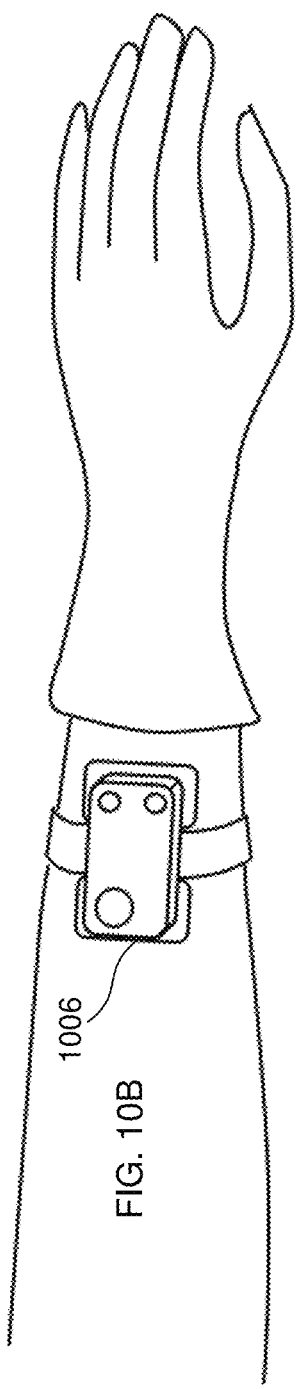
FIG. 10B shows the device coupled to the alignment bracket with a portion of the device making contact with the skin through the aperture.
Figure 10C:
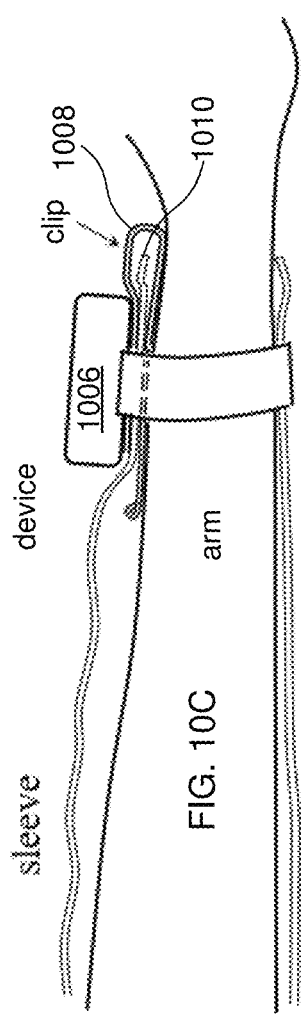
FIG. 10C shows a conductive clip attached to the device and configured to slide over the end of the cuff, allowing for electrical contact to the skin

The electrostatic mitigation device may be implemented where users also wear protective clothing (smocks or coveralls, and gloves) which is expected to cover all bare skin. This might prevent electrical contact between the device and the user's skin. One solution is to modify the sleeves of the protective garments at the wrist area by providing a mounting or alignment bracket, and an aperture through the garment material, so that when the device is placed in the bracket its base is aligned with the aperture and can make contact with the skin through the aperture (e.g., FIGS. 10A and 10B). Alternatively, the device could be provided with a conductive clip that slides under the cuff of the protective garment, allowing for full skin coverage and yet maintaining electrical contact with the skin (e.g., FIG. 10C). FIG. 10A shows the sleeve of a smock provided with an alignment bracket 1002 and two apertures 1004 through to the skin, and FIG. 10B shows the device 1006 coupled to the alignment bracket 1002 with a portion of the device 1006 making contact with the skin through the apertures 1004 (though mere proximity rather than contact is needed since field measurements are being made). FIG. 10C shows a conductive clip 1008 attached to the device 1006 and configured to slide over the end 1010 of the cuff, allowing for electrical contact to the skin. Although a glove has not been illustrated in FIG. 10C for the sake of clarity, it can be perceived that a properly designed clip 1008 would allow the glove to be worn over the clip 1008 and the end 1010 of the cuff, thereby providing full skin coverage while still enabling a conductive path between the device 1006 and the user's skin. Although a clip 1008 around a cuff of the garment is shown in FIG. 10, in other embodiments, the clip 1008 could wrap around any edge of the garment (e.g., a bottom edge of the torso or a collar to name two non-limiting examples). A further alternative arrangement is that the wearer could use a conventional tether-type wrist strap, which instead of being conductively connected to the bench would be conductively connected to the device, and form the skin contact terminal of the device (e.g., 312 or 314). This has the advantage that in workplaces where tethers are worn, it does not require any change in e.g., clothing or other ESD-related practices, but the worker is freed up from the tether restriction.

In an embodiment, the electrostatic charge mitigation device can include a non-transitory, tangible computer readable storage medium, encoded with processor readable instructions to perform a method for mitigating electrostatic potential on a user's body without a grounding connection. The method can include sensing an electrostatic potential of the body relative to the surrounding atmosphere and surrounding objects. The method can further include identifying when the electrostatic potential of the body reaches a threshold. The method can further include generating a voltage between an ion gun and an electrode coupled to the body that is large enough to initiate ion discharge from the ion gun, the polarity of the discharge selected to reduce the electrostatic potential of the body. Finally, the method can include modifying the sensing after the ion discharge to reduce sensing artefacts caused by the ion discharge.

Figure 13:
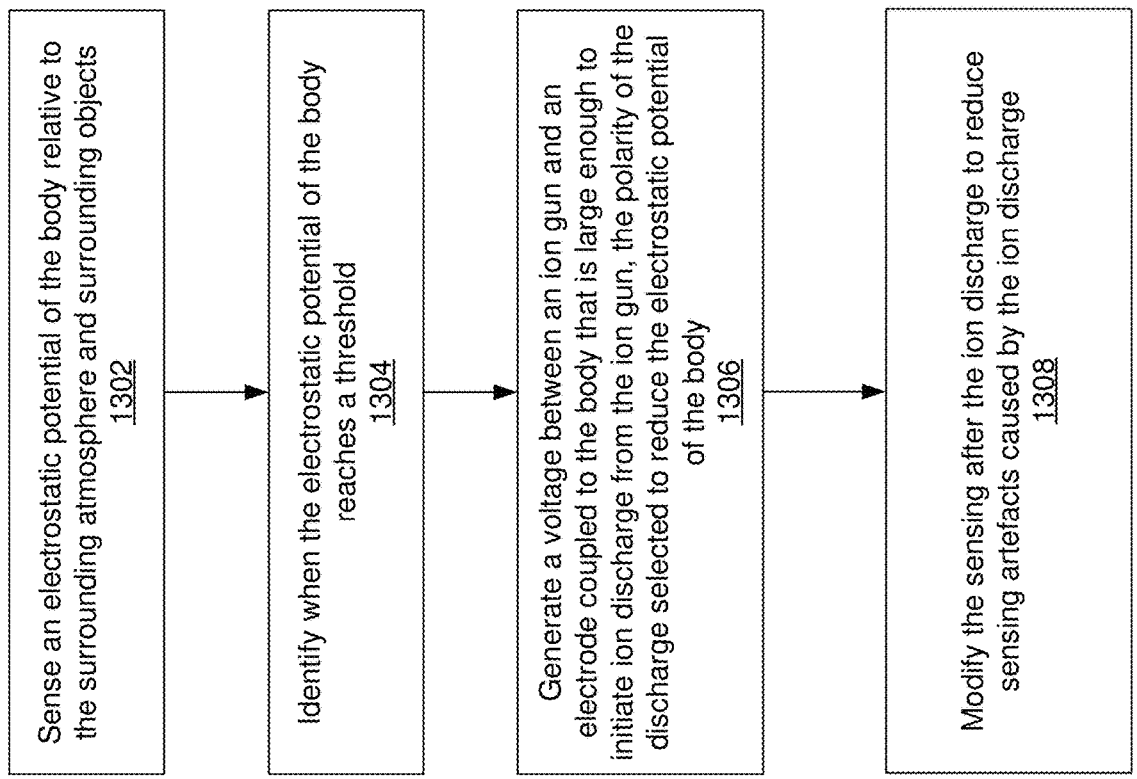
FIG. 13 illustrates an embodiment of a method to mitigate electrostatic charge buildup without a grounding connection.

FIG. 13 illustrates a method for mitigating electrostatic potential on a user's body without a grounding connection. The method 1300 can include sensing an electrostatic potential of the body relative to the surrounding atmosphere and surrounding objects (Block 1302). The method 1300 can further include identifying when the electrostatic potential of the body reaches a threshold (Block 1304). The method 1300 can further include generating a voltage between an ion gun and an electrode coupled to the body that is large enough to initiate ion discharge from the ion gun, the polarity of the discharge selected to reduce the electrostatic potential of the body (Block 1304). Finally, the method 1300 can include modifying the sensing after the ion discharge to reduce sensing artefacts caused by the ion discharge (Block 1306).

Figure 14:
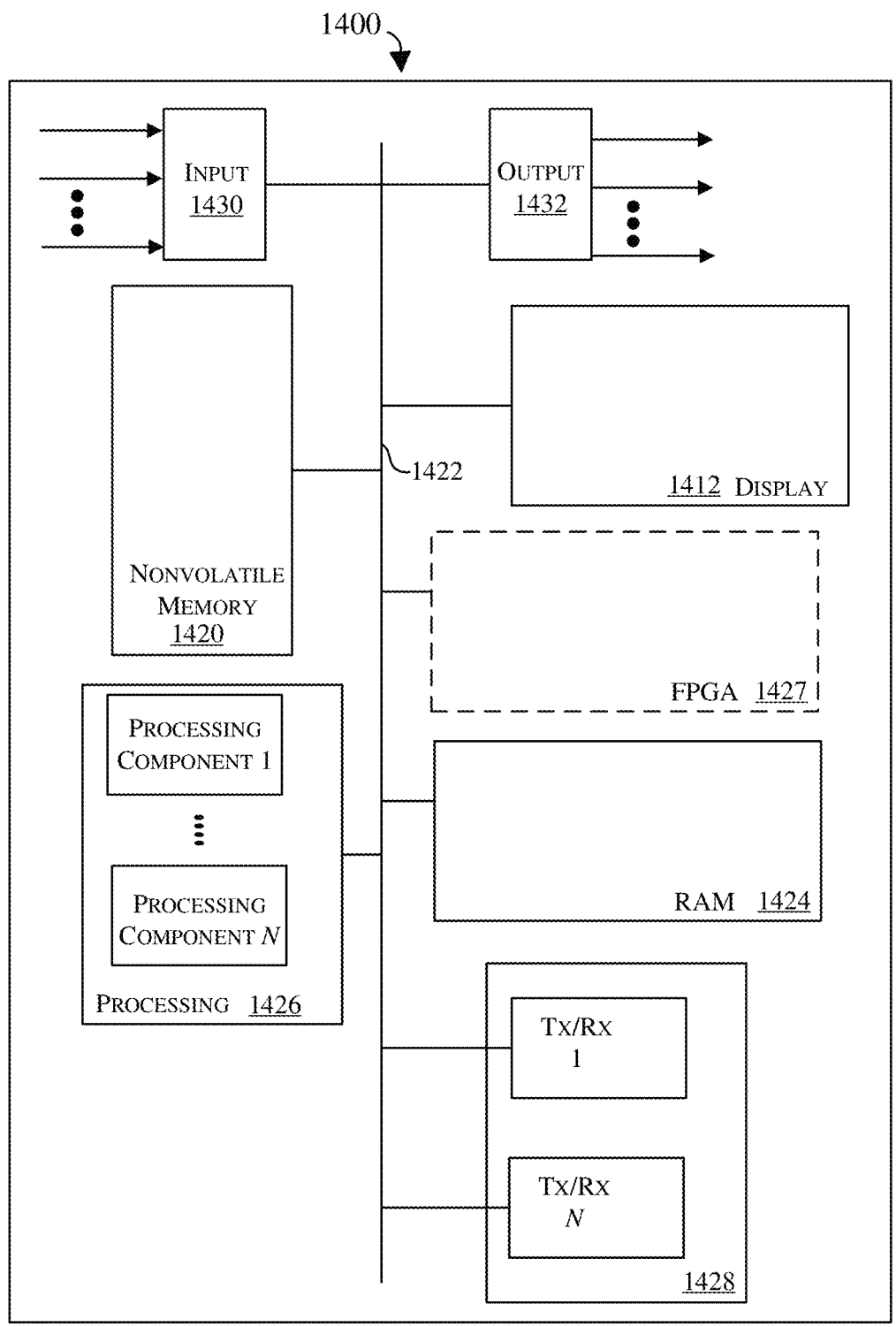
FIG. 14 shows a block diagram depicting physical components that may be utilized to realize controllers according to an exemplary embodiment.

The methods described in connection with the embodiments disclosed herein may be embodied directly in hardware, in processor-executable code encoded in a non-transitory tangible processor readable storage medium, or in a combination of the two. Referring to FIG. 14 for example, shown is a block diagram depicting physical components that may be utilized to realize the control 304 and the control processor 1400 according to an exemplary embodiment. As shown, in this embodiment a display portion 1412 and nonvolatile memory 1420 are coupled to a bus 1422 that is also coupled to random access memory ("RAM") 1424, a processing portion (which includes N processing components) 1426, an optional field programmable gate array (FPGA) 1427, and a transceiver component 1428 that includes N transceivers, which may be wireless. Although the components depicted in FIG. 14 represent physical components, FIG. 14 is not intended to be a detailed hardware diagram; thus, many of the components depicted in FIG. 14 may be realized by common constructs or distributed among additional physical components. Moreover, it is contemplated that other existing and yet-to-be developed physical components and architectures may be utilized to implement the functional components described with reference to FIG. 14.

This display portion 1412 generally operates to provide a user interface for a user, and in several implementations, the display is realized by a touchscreen display. In general, the nonvolatile memory 1420 is non-transitory memory that functions to store (e.g., persistently store) data and processor-executable code (including executable code that is associated with effectuating the methods described herein). In some embodiments for example, the nonvolatile memory 1420 includes bootloader code, operating system code, file system code, and non-transitory processor-executable code to facilitate the execution of a method described with reference to FIGS. 7 and 13 described further herein.

In many implementations, the nonvolatile memory 1420 is realized by flash memory (e.g., NAND or ONENAND memory), but it is contemplated that other memory types may be utilized as well. Although it may be possible to execute the code from the nonvolatile memory 1420, the executable code in the nonvolatile memory is typically loaded into RAM 1424 and executed by one or more of the N processing components in the processing portion 1426.

The N processing components in connection with RAM 1424 generally operate to execute the instructions stored in nonvolatile memory 1420 to enable electrostatic charge mitigation via ion discharge. For example, non-transitory, processor-executable code to effectuate the methods described with reference to FIGS. 7 and 13 may be persistently stored in nonvolatile memory 1420 and executed by the N processing components in connection with RAM 1424. As one of ordinarily skill in the art will appreciate, the processing portion 1426 may include a video processor, digital signal processor (DSP), micro-controller, graphics processing unit (GPU), or other hardware processing components or combinations of hardware and software processing components (e.g., an FPGA or an FPGA including digital logic processing portions).

In addition, or in the alternative, the processing portion 1426 may be configured to effectuate one or more aspects of the methodologies described herein (e.g., the methods described with reference to FIGS. 7 and 13). For example, non-transitory processor-readable instructions may be stored in the nonvolatile memory 1420 or in RAM 1424 and when executed on the processing portion 1426, cause the processing portion 1426 to perform a method for sensing electrostatic buildup that exceeds a threshold and then using positive or negative ion discharge to reduce the buildup to acceptable levels. Alternatively, non-transitory FPGA-configuration-instructions may be persistently stored in nonvolatile memory 1420 and accessed by the processing portion 1426 (e.g., during boot up) to configure the hardware-configurable portions of the processing portion 1426 to effectuate the functions of the control section 304 or the control processor 1100.

The input component 1430 operates to receive signals (e.g., the electrostatic charge sensed at the sensing section 302 or the electric field sensor(s) 1108) that are indicative of one or more aspects of the charge buildup on the user's body. The signals received at the input component may include, for example, a voltage, current, or digital signal, depending on the type of sensor or sensing section used. The output component generally operates to provide one or more analog or digital signals to effectuate control of the discharge section and optionally switches 322 and 320. For example, the output portion 1432 may provide the control signals described with reference to FIG. 5.

The depicted transceiver component 1428 includes N transceiver chains, which may be used for communicating with external devices via wireless or wireline networks. Each of the N transceiver chains may represent a transceiver associated with a particular communication scheme (e.g., WiFi, Ethernet, Profibus, etc.).

The use of wireless communication enables the devices disclosed here to be located in space through their communication with fixed wireless base stations of known locality (for example, if the wireless communication technology used is the Bluetooth Low Energy 5.1 standard, location services are an integral part of the communication protocol). This enables the devices to be used to map out, within a factory floor or manufacturing facility, those areas where there are "hot spots" or high occurrence of ESD events or even high density of charge. This is performed by communicating from the device to a central processor the location of the device, together with information about the accumulation of charge on the wearer and/or the necessity to discharge the wearer.

Some portions are presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm is a self-consistent sequence of operations or similar processing leading to a desired result. In this context, operations or processing involves physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The terms and expressions employed herein are used as terms and expressions of description and not of limitation, and there is no intention, in the use of such terms and expressions, of excluding any equivalents of the features shown and described or portions thereof. Each of the various elements disclosed herein may be achieved in a variety of manners. This disclosure should be understood to encompass each such variation, be it a variation of an embodiment of any apparatus embodiment, a method or process embodiment, or even merely a variation of any element of these. Particularly, it should be understood that the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled.

As but one example, it should be understood that all action may be expressed as a means for taking that action or as an element which causes that action. Similarly, each physical element disclosed should be understood to encompass a disclosure of the action which that physical element facilitates. Regarding this last aspect, by way of example only, the disclosure of a "protrusion" should be understood to encompass disclosure of the act of "protruding"—whether explicitly discussed or not—and, conversely, were there only disclosure of the act of "protruding", such a disclosure should be understood to encompass disclosure of a "protrusion". Such changes and alternative terms are to be understood to be explicitly included in the description.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

As used herein, the recitation of "at least one of A, B and C" is intended to mean "either A, B, C or any combination of A, B and C." The previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

What is claimed is:

1. An electrostatic mitigation device without a direct grounding connection comprising:
    a sensing section that is physically attached to a user's body;
    a discharge section conductively coupled via an electrode to a user's body;
    a controller coupled to both the sensing section and the discharge section, and configured to, when the sensing section detects an absolute electrostatic potential between the user's body and a surrounding environment, and one or more objects within the surrounding environment, exceeding a threshold, instructing the discharge section to emit positive or negative ions of equal polarity to the absolute electrostatic potential to remove charge from the user's body until the absolute electrostatic potential falls below the threshold.

2. The electrostatic mitigation device of claim 1, wherein the sensing section comprises a miniaturized electric field mill.

3. The electrostatic mitigation device of claim 2, wherein the miniaturized electric field mill comprises sense electrodes fabricated as a thin conductive film on a dielectric or insulating substrate and a rotating shutter.

4. The electrostatic mitigation device of claim 3, wherein the miniaturized electric field mill comprises a conductive shield driven to the same potential as the sense electrodes.

5. The electrostatic mitigation device of claim 1, wherein the discharge section comprises a high voltage source inductively coupled to the electrode and inductively and capacitively coupled to a discharge electrode.

6. The electrostatic mitigation device of claim 1, wherein the electrode is formed as a part of a garment, passes through the garment, or is coupled to a conductive clip that wraps around an edge of the garment.

7. The electrostatic mitigation device of claim 1, wherein the sensing section is in conductive communication with the user's body.

8. The electrostatic mitigation device of claim 1, further comprising one or more switches or variable-resistance components arranged between the sensing section and the electrode and configured to open or increase resistance during ion discharge by the discharge section.

9. The electrostatic mitigation device of claim 1, wherein the sensing section is distributed between two or more sensors spaced apart on the user's body.

10. The electrostatic mitigation device of claim 1, further comprising a forced air component, a charged grid acceleration component, or an electrodynamic streaming component, any of these configured to enhance movement of the positive or negative ions away from the user's body.

11. The electrostatic mitigation device of claim 1, further comprising a wireless transceiver configured to communicate with at least one fixed antenna of known location to map ESD hot spots.

12. An electrostatic mitigation device without a direct grounding connection comprising:

a means to detect electrostatic potential of a user's body, to which the device is coupled, relative to an absolute electrostatic potential of nearby objects;

a means to discharge at least a portion of the electrostatic potential of the user's body by expelling positive or negative ions to a surrounding environment;

an electrode coupled between the user's body and the means to discharge; and wherein the means to detect electrostatic potential also detects electrostatic potential of the user's body, to which the device is coupled, relative to an average electrostatic potential of the surrounding environment.

13. The electrostatic mitigation device of claim 12, wherein the electrode is formed as a part of a garment, passes through the garment, or is coupled to a conductive clip that wraps around an edge of the garment.

14. The electrostatic mitigation device of claim 12, further comprising two or more electrostatic shields and resistive links between the two or more electrostatic shields configured to reduce conduction between the two or more electrostatic shields.

15. The electrostatic mitigation device of claim 12, further comprising one or more switches or variable-resistance components to fully or partially isolate the means to detect electrostatic potential from the means to discharge at least a portion of the electrostatic potential during the expelling of positive or negative ions.

16. The electrostatic mitigation device of claim 12, wherein the means to detect electrostatic potential comprises two or more sensors arranged at different locations on the user's body.

17. The electrostatic mitigation device of claim 16, wherein the means to detect electrostatic potential comprises two or more miniaturized electric field mills each with sense electrodes deposited as a thin film on a substrate in close proximity to and electrically coupled to an amplifier.

18. The electrostatic mitigation device of claim 17, wherein the two or more miniaturized electric field mills further comprise a conductive shield driven to the same potential as the sense electrodes.

19. The electrostatic mitigation device of claim 12, further comprising a forced air component, a charged grid acceleration component, or an electrodynamic streaming component, any of these configured to enhance movement of the positive or negative ions away from the user's body.

20. The electrostatic mitigation device of claim 12, further comprising a wireless transceiver configured to communicate with at least one fixed antenna of known location to map ESD hot spots.

21. A method of maintaining a body below an electrostatic potential without a grounding connection, the method comprising:

sensing an electrostatic potential of the body relative to the surrounding atmosphere and surrounding objects;

identifying when the electrostatic potential of the body reaches a threshold; and then generating a voltage between an ion gun and an electrode coupled to the body that is large enough to initiate ion discharge from the ion gun, the polarity of the discharge selected to reduce the electrostatic potential of the body relative to the surrounding atmosphere and surrounding objects; and modifying the sensing after the ion discharge to reduce sensing artefacts caused by the ion discharge.

22. The method of claim 21, further comprising applying a force to the ion discharge to direct ions away from the body.

23. The method of claim 21, wherein the force is generated by a forced air component; a charged grid acceleration component; and an electrodynamic streaming component.

24. The method of claim 21, wherein a device for performing the sensing and a device for performing the ion gun are separated on the body.

25. The method of claim 21, further comprising following each primary positive discharge pulse or primary negative discharge pulse with an opposite polarity anti-shot pulse having a duration of less than 20% of the primary positive/negative discharge pulse, so that the primary positive discharge pulse or primary negative discharge pulse maintains sufficient charge transfer to be meaningful.

26. The method of claim 21, further comprising compensating for artefacts detected during the sensing that are caused by the ion discharge rather than the electrostatic potential of the body relative to the surrounding atmosphere and surrounding objects.

27. The method of claim 21, further comprising mapping ESD hot spots via communication with at least one fixed antenna having a known location.

\* \* \* \* \*